United States Patent
Christ et al.

(10) Patent No.: US 11,324,857 B2
(45) Date of Patent: May 10, 2022

(54) METHODS FOR MAKING A TISSUE ENGINEERED MUSCLE REPAIR (TEMR) CONSTRUCT IN VITRO FOR IMPLANTATION IN VIVO

(71) Applicant: Wake Forest University Health Sciences, Winston-Salem, NC (US)

(72) Inventors: George J. Christ, Crozet, VA (US); Benjamin T. Corona, Converse, TX (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/378,534

(22) Filed: Dec. 14, 2016

(65) Prior Publication Data

US 2017/0087278 A1    Mar. 30, 2017

Related U.S. Application Data

(60) Division of application No. 13/765,104, filed on Feb. 12, 2013, now Pat. No. 9,556,418, which is a continuation of application No. PCT/US2011/047600, filed on Aug. 12, 2011.

(60) Provisional application No. 61/373,624, filed on Aug. 13, 2010.

(51) Int. Cl.
```
A61L 27/38      (2006.01)
A61K 35/34      (2015.01)
A61F 2/08       (2006.01)
A61K 35/12      (2015.01)
C12N 5/077      (2010.01)
C12M 1/42       (2006.01)
C12N 5/071      (2010.01)
```

(52) U.S. Cl.
CPC ............ *A61L 27/3895* (2013.01); *A61F 2/08* (2013.01); *A61K 35/34* (2013.01); *A61L 27/3826* (2013.01); *A61L 27/3873* (2013.01); *C12M 35/02* (2013.01); *C12N 5/0658* (2013.01); *C12N 5/0697* (2013.01); *A61F 2002/0894* (2013.01); *A61K 35/12* (2013.01); *C12N 2527/00* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 4,839,280 A | 6/1989 | Banes | |
| 4,910,138 A | 3/1990 | Miura | |
| 4,940,853 A | 7/1990 | Vandenburgh | |
| 5,348,879 A | 9/1994 | Shapiro | |
| 5,406,853 A | 4/1995 | Lintilhac et al. | |
| 5,573,784 A | 11/1996 | Badylak et al. | |
| 5,695,996 A | 12/1997 | Quinn et al. | |
| 5,750,329 A | 5/1998 | Quinn et al. | |
| 5,773,285 A | 6/1998 | Park | |
| 5,795,710 A | 8/1998 | Park | |
| 5,858,783 A | 1/1999 | Goodwin et al. | |
| 6,051,750 A | 4/2000 | Bell | |
| 6,057,150 A | 5/2000 | Lee et al. | |
| 6,107,081 A | 8/2000 | Feeback et al. | |
| 6,162,642 A | 12/2000 | Redbrake-Adams et al. | |
| 6,206,931 B1 | 3/2001 | Cook et al. | |
| 6,214,021 B1 | 4/2001 | Hadlock et al. | |
| 6,472,202 B1 | 10/2002 | Banes | |
| 6,479,064 B1 | 11/2002 | Atala | |
| 6,485,723 B1 | 11/2002 | Badylak et al. | |
| 6,554,857 B1 | 4/2003 | Zilla et al. | |
| 6,576,457 B1 | 6/2003 | Hua | |
| 6,592,623 B1 * | 7/2003 | Bowlin | A61F 2/08 623/13.17 |
| 6,596,296 B1 | 7/2003 | Nelson et al. | |
| 6,645,759 B2 | 11/2003 | Banes | |
| 6,673,108 B2 | 1/2004 | Zilla et al. | |
| 6,743,435 B2 | 6/2004 | De Vore et al. | |
| 6,962,814 B2 | 11/2005 | Mitchell et al. | |
| 6,998,418 B1 | 2/2006 | Sung et al. | |

(Continued)

FOREIGN PATENT DOCUMENTS

| WO | WO 00/34442 | 6/2000 |
|---|---|---|
| WO | WO 2006/113382 A2 | 10/2006 |
| WO | WO 2012/021814 A2 | 2/2012 |

OTHER PUBLICATIONS

Candiani et al. "Cyclic mechanical stimulation favors myosin heavy chain accumulation in engineered skeletal muscle constructs", Journal of Applied Biomaterials & Biomechanics 8(2): 68-75, 2010 (Year: 2010).*

(Continued)

*Primary Examiner* — Emily A Cordas
(74) *Attorney, Agent, or Firm* — Myers Bigel, P.A.

(57) ABSTRACT

Provided herein are methods of culturing organized skeletal muscle tissue from precursor muscle cells by cyclically stretching and relaxing said muscle cells on a support in vitro for a time sufficient to produce said organized skeletal muscle tissue, including reseeding said organized skeletal muscle tissue by contacting additional precursor muscle cells to said organized skeletal muscle tissue on said solid support, and then repeating said step of cyclically stretching and relaxing said muscle cells in said support in vitro for time sufficient to enhance the density (i.e., increased number of nuclei and/or number of multinucleated cells) of said organized skeletal muscle tissue on said support.

14 Claims, 17 Drawing Sheets

(56) References Cited

U.S. PATENT DOCUMENTS

| | | | |
|---|---|---|---|
| 7,157,428 B2 | 1/2007 | Kusanagi et al. | |
| 7,163,920 B2 | 1/2007 | Dhanaraj et al. | |
| 7,195,774 B2 | 3/2007 | Carvalho et al. | |
| 7,468,192 B2 | 12/2008 | Mizuno et al. | |
| 7,560,432 B2 | 7/2009 | Kusanagi et al. | |
| 7,563,280 B2 | 7/2009 | Anderson et al. | |
| 7,604,663 B1 | 10/2009 | Reimink et al. | |
| 8,815,584 B1* | 8/2014 | Hickman | C12N 5/0619 435/373 |
| 2002/0072798 A1 | 6/2002 | Riesle et al. | |
| 2002/0142458 A1 | 10/2002 | Williams et al. | |
| 2002/0142459 A1 | 10/2002 | Williams et al. | |
| 2002/0151968 A1 | 10/2002 | Zilla et al. | |
| 2003/0064088 A1 | 4/2003 | Carvalho et al. | |
| 2003/0017541 A1 | 9/2003 | Campbell et al. | |
| 2004/0063206 A1 | 4/2004 | Rowley et al. | |
| 2004/0134502 A1 | 7/2004 | Mizuno et al. | |
| 2004/0147016 A1 | 7/2004 | Rowley et al. | |
| 2004/0151705 A1 | 8/2004 | Mizuno et al. | |
| 2005/0009178 A1 | 1/2005 | Yost et al. | |
| 2005/0028228 A1 | 2/2005 | McQuillan et al. | |
| 2005/0038520 A1 | 2/2005 | Binette et al. | |
| 2005/0043813 A1 | 2/2005 | Kusanagi et al. | |
| 2005/0043814 A1 | 2/2005 | Kusanagi et al. | |
| 2005/0074877 A1 | 4/2005 | Mao | |
| 2005/0125077 A1 | 6/2005 | Harmon et al. | |
| 2005/0187162 A1 | 8/2005 | Dhanaraj et al. | |
| 2005/0197304 A1 | 9/2005 | DiCesare | |
| 2005/0222688 A1 | 10/2005 | Zilla et al. | |
| 2006/0069011 A1 | 3/2006 | Kusanagi et al. | |
| 2006/0083728 A1 | 4/2006 | Kusanagi et al. | |
| 2006/0134050 A1 | 6/2006 | Griffith et al. | |
| 2006/0160734 A1 | 7/2006 | Kusanagi et al. | |
| 2006/0188488 A1 | 8/2006 | Williams et al. | |
| 2006/0195179 A1 | 8/2006 | Sun et al. | |
| 2006/0216822 A1 | 9/2006 | Mizuno et al. | |
| 2006/0239981 A1 | 10/2006 | Yoo et al. | |
| 2007/0014867 A1 | 1/2007 | Kusanagi et al. | |
| 2007/0087033 A1 | 4/2007 | Sigg et al. | |
| 2007/0104692 A1 | 5/2007 | Quijano et al. | |
| 2007/0162121 A1 | 7/2007 | Tarrant et al. | |
| 2007/0184033 A1 | 8/2007 | Sevrain et al. | |
| 2007/0249044 A1 | 10/2007 | Desai et al. | |
| 2008/0009942 A1 | 1/2008 | Mizuno et al. | |
| 2008/0020049 A1 | 1/2008 | Darling et al. | |
| 2008/0193910 A1* | 8/2008 | Larkin | A61L 27/3834 435/1.1 |
| 2008/0195229 A1 | 8/2008 | Quijano et al. | |
| 2008/0274185 A1 | 11/2008 | Mao | |
| 2009/0214614 A1 | 8/2009 | Everland et al. | |
| 2009/0220569 A1 | 9/2009 | Williams et al. | |
| 2009/0246247 A1 | 10/2009 | Shetty et al. | |
| 2009/0252798 A1 | 10/2009 | Kaps et al. | |
| 2009/0265005 A1 | 10/2009 | Yoo et al. | |
| 2010/0047316 A1 | 2/2010 | Hendriks et al. | |
| 2010/0111938 A1 | 5/2010 | Boyden et al. | |
| 2010/0112014 A1 | 5/2010 | Gilbert et al. | |
| 2010/0112067 A1 | 5/2010 | Boyden et al. | |
| 2010/0120149 A1 | 5/2010 | Kim et al. | |

OTHER PUBLICATIONS

Riboldi et al. "Skeletal myogenesis on highly orientated microfibrous polyesterurethane scaffolds." Journal of Biomedical Materials Research Part A: An Official Journal of the Society for Biomaterials, 84.4 (2008): 1094-1101. (Year: 2008).*
Kummer et al. "Nerve-independent formation of a topologically complex postsynaptic apparatus." The Journal of Cell Biology 164.7 (2004): 1077-1087 (Year: 2004).*
Office Action, Canadian Intellectual Property Office Examination Report, Canadian Patent Application No. 2,807,762, dated Apr. 28, 2017, 6 pp.
Teressa G and Prives J. Cell culture-based analysis of postsynaptic membrane assembly in muscle cells. Biological Procedures Online. Dec. 2008; 10(1): 58-65.
Cartwright LM et al. Porcine bladder acellular matrix porosity: Impact of hyaluronic acid and lyophilization. Journal of Biomedical Material Research. 2006; 77A(1): 180-184.
Campion D.R., "The Muscle Satellite Cell: A Review", *International Review of Cytology*, vol. 87, 1984, pp. 225-251 (Abstract Only).
Clarke et al., "Mechanical load induces sarcoplasmic wounding and FGF release in differentiated human skeletal muscle cultures", *FASEB J.*, 10: 502-509, 1996.
Dahms et al., "Composition and biomechanical properties of the bladder acellular matrix graft: comparative analysis in rat, pig and human", *British Journal of Urology*, 1998, 82: 411-419.
European Examination Report, EP 06750099, dated Jul. 31, 2009.
Flynn L. et al., "Fiber templating of poly(2-hydroxyethyl methacrylate) for neural tissue engineering", *Biomaterials*, 24 (2003), 4265-4272.
Ghaghada K.B. et al., "Folate targeting of drug carriers: A mathematical model", *Journal of Controlled Release*, vol. 104, Issue 1, May 5, 2005, pp. 113-128.
Grinnell F. et al. Dendritic fibroblasts in three-dimensional collagen matrices. *Molecular Biology of the Cell*, Feb. 2003; 14: 384-395.
Hurme T. et al., "Healing of skeletal muscle injury: an ultrastructural and immunohistochemical study", *Medicine & Science in Sports & Exercise*, vol. 23(7): 801-810, Jul. 1991 (Abstract Only).
International Preliminary Report on Patentability Corresponding to International Application No. PCT/US2011/047600; dated Mar. 28, 2013; 6 Pages.
International Search Report and Written Opinion for PCT/US06/13963; dated Nov. 29, 2006.
Larkin L.M. et al., "Functional Evaluation of Nerve-Skeletal Muscle Constructs Engineered In Vitro", *In Vitro Cell. Dev. Biol.—Animal*, 42:75-82, Mar. and Apr. 2006.
Liao H. et al., "Development and Progress of Engineering of Skeletal Muscle Tissue", *Tissue Engineering Part B*, vol. 15, No. 3, 2009, pp. 319-331.
Linnes M.P. et al., "A fibrinogen-based precision microporous scaffold for tissue engineering", *Biomaterials*, 28 (2007), 5298-5306.
Machingal M.A. et al., "A Tissue-Engineered Muscle Repair Construct for Functional Restoration of an Irrecoverable Muscle Injury in a Murine Model", *Tissue Engineering: Part A*, vol. 17, Nos. 17 and 18, 2011, 2291-2303.
Moon S.G. et al., Cyclic mechanical preconditioning improves engineered muscle contraction. *Tissue Engineering: Part A*. 2008; 14(4): 473-482.
Saul J. M. et al., "A dual-ligand approach for enhancing targeting selectivity of therapeutic nanocarriers", *Journal of Controlled Release*, vol. 114, Issue 3, Sep. 12, 2006, pp. 277-287.
Saul J. M. et al., "Delivery of non-viral gene carriers from sphere-templated fibrin scaffolds for sustained transgene expression", *Biomaterials*, vol. 28, Issue 31, Nov. 2007, pp. 4705-4716 (Abstract Only).
Saul J.M. et al., "Multilayer Nanocomplexes of Polymer and DNA Exhibit Enhanced Gene Delivery", *Advanced Materials*, 2008, vol. 20, 19-25.
Stegemann J.P. and Nerem R.M. "Phenotype modulation in vascular tissue engineering using biochemical and mechanical stimulation" *Annals of Biomedical Engineering*. 2003; 31(4): 391-402.
Stokols S. et al., "Templated Agarose Scaffolds Support Linear Axonal Regeneration", *Tissue Engineering*, vol. 12, No. 10, 2006, 2777-2787.
Supplementary European Search Report, EP 06750099, dated Apr. 21, 2009.
Tatsumi et al., "Mechanical stretch Induces Activation of Skeletal Muscle Satellite Cells in Vitro", *Experimental Cell Research*, 267: 107-114, 2001.
Vandenburgh et al., "In vitro Model for Stretch-Induced Hypertrophy of Skeletal Muscle", *Science*, 203: 265-268, 1979.
Vandenburgh H.H.. A computerized mechanical cell stimulator for tissue culture: effects on skeletal muscle organogenesis. In Vitro Cellular & Developmental Biology. Jul. 1988; 24(7): 609-619.
Waters et al., "A system to impose prescribed homogenous strains on cultured cells", *J. Appl. Physiol.*, 91: 1600-1610, 2001.

(56) References Cited

OTHER PUBLICATIONS

Supplementary European Search Report and Opinion, EP 12835869, dated Sep. 10, 2015.
Daggett DF et al. The role of an agrin-growth factor interaction in ACh receptor clustering. Molecular and Cellular Neuroscience. 1996; 8: 272-285.
Kim S et al. NGL family PSD-95-interacting adhesion molecules regulate excitatory synapse formation. Nature Neuroscience. Oct. 2006; 9(10): 1294-1301.
Glass DJ et al. Agrin acts via a MuSK receptor complex. Cell. May 17, 1996; 85: 513-523.
Supplementary European Search Report, EP 11817111, dated Mar. 6, 2014.
Powell CA et al. Mechanical stimulation improves tissue-engineered human skeletal muscle. Am J Physiol Cell Physiol. Jul. 17, 2002; 283(5); C1557-C1565.
Kobayashi N et al. Mechanical stress promotes the expression of smooth muscle-like properties in marrow stromal cells. Experimental Hematology. Dec. 1, 2004; 32(12): 1238-1245.
Moon DG et al. Cyclic mechanical preconditioning improves engineered muscle contraction. Tissue Engineering: Part A. 473-482 14(4): 473-482, 2008.
Grubic Z et al. Myoblast fusion and innervation with rat motor nerve alter distribution of acetylcholinesterase and its mRNA in cultures of human muscle. Neuron. Feb. 1995; 14: 317-327.
Kobayashi N et al. Acetylcholine receptors and acetylcholinesterase accumulate at the nerve-muscle contacts of de novo grown human monolayer muscle cocultures with fetal rat spinal cord. Experimental Neurology. May 1, 1985; 88(2): 327-335.
Machingal MA et al. A tissue-engineered muscle repair construct for functional restoration of an irrecoverable muscle injury in a murine model. Tissue Engineering: Part A. Jul. 28, 2011. 17(17-18): 2291-2303.
Corona BT et al. Further development of a tissue engineered muscle repair construct in vitro for enhanced functional recovery following implantation in vivo in a murine model of volumetric muscle loss injury. Tissue Engineering: Part A. Jun. 1, 2012; 18 (11-12): 1213-1228.
Canadian Intellectual Property Office Examination Report, Canadian Patent Application No. 2,807,762, dated Jun. 19, 2019, 4 pages.
Canadian Office Action corresponding to CA 2,807,762; dated Jul. 31, 2020 (4 pp).
Canadian Office Action corresponding to CA 2,807,762; dated Nov. 2, 2021 (5 pages).

\* cited by examiner

METHODS FOR MAKING A TISSUE ENGINEERED MUSCLE REPAIR (TEMR) CONSTRUCT IN VITRO FOR IMPLANTATION IN VIVO

This application is a divisional of and claims priority to U.S. patent application Ser. No. 13/765,104, filed Feb. 12, 2013, now U.S. Pat. No. 9,556,418, which is a continuation application of PCT Application No. PCT/US2011/047600, filed Aug. 12, 2011, which in turn claims the benefit of U.S. Provisional Application No. 61/373,624, filed Aug. 13, 2010, the disclosures of each of which are incorporated by reference herein in their entirety.

STATEMENT OF GOVERNMENT SUPPORT

This invention was made with Government support under contract W81XWH-09-1-0578 from the Department of Defense. The United States Government has certain rights to this invention.

FIELD OF THE INVENTION

The present invention concerns methods and apparatus for the growth of skeletal muscle in vitro.

BACKGROUND OF THE INVENTION

Volumetric muscle loss due to a variety of causes, including congenital and acquired conditions, invasive surgical procedures, and traumatic injury, produces a physiological deficit for which there are currently no effective clinical treatments. Management involves the use of existing host tissue to construct muscular flaps or grafts. However, this approach is not always feasible, delaying the rehabilitation process and restoration of tissue function. The ability to create clinically relevant autologous tissue engineered muscle repair (TEMR) constructs in vitro for restoration of muscle mass and function in vivo would remove a major hurdle to the successful skeletal muscle reconstructive procedures required to repair complex extremity and facial injuries suffered by injured individuals. See, e.g., Yoo et al., US Patent Application Publication No. US2006/0239981 (Oct. 26, 2006).

SUMMARY OF THE INVENTION

Provided herein are methods of culturing organized skeletal muscle tissue from precursor muscle cells by cyclically stretching and relaxing said muscle cells on a support in vitro for a time sufficient to produce said organized skeletal muscle tissue, including reseeding said organized skeletal muscle tissue by contacting additional precursor muscle cells to said organized skeletal muscle tissue on said solid support, and then repeating said step of cyclically stretching and relaxing said muscle cells in said support in vitro for time sufficient to enhance the density (i.e., increased number of nuclei and number of multinucleated cells) of said organized skeletal muscle tissue on said support.

In some embodiments, the reseeding step is carried out under static conditions. In some embodiments, the reseeding step is carried out by contacting a solution carrying precursor muscle cells to said organized skeletal muscle tissue for a time of 10 minutes to two days.

In some embodiments, the reseeding step is carried out by contacting a solution carrying precursor muscle cells to said organized skeletal muscle tissue inside a mold configured to confine a cell suspension on top of one or more of the supports and/or supports seeded with cells.

In some embodiments, the cyclically stretching and relaxing said muscle cells on a support in vitro comprises: (a) providing precursor muscle cells on a support in a tissue media; then (b) cyclically stretching and relaxing said support at least twice along a first axis during a first time period; and then (c) maintaining said support in a substantially static position during a second time period; and then (d) repeating steps (b) and (c) for a number of times sufficient to enhance the functionality of the muscle tissue or produce organized skeletal muscle tissue on said solid support from said precursor muscle cells (e.g., increase the number of multinucleated cells, increase myotube width, enhance cellular alignment or orientation along an axis, etc.).

In some embodiments, the cyclically stretching and relaxing is carried out at least three times (e.g., from 3 or 4 to 10 or 20 times) during said first time period.

In some embodiments, the stretching comprises extending said support to a dimension between 5% and 15% greater in length than said static position. In some embodiments, the stretching comprises extending said support to a dimension of between 8% and 12% greater in length than said static position.

In some embodiments, the first time period is from 2 to 10 minutes in duration; and wherein said second time period is from 5 to 40 minutes in duration. In some embodiments, the repeating of steps (b) and (c) is carried out for a time of five days to three weeks. In some embodiments, the reseeding step is repeated one, two, three, four or five or more times.

Multi-layered skeletal muscle tissues produced by the processes disclosed herein are also provided. In some embodiments, the tissue comprises elongated multi-nucleated muscle fibers or cells (e.g., from 5, 0 or 15 to 100, 200, or 400 multinucleated cells per square millimeter of tissue or support surface area). In some embodiments, the tissue expresses acetylcholine (ACh) receptors (e.g., aggregated ACh receptors). In some embodiments, the tissue is suturable. In some embodiments, the construct further comprises or includes activated satellite cells or myoblasts.

Also provided are methods of treating a skeletal muscle injury in a patient in need thereof comprising grafting a skeletal muscle tissue (e.g., produced by the processes disclosed herein) into said patient in a treatment-effective configuration. Further provided is the use of a skeletal muscle tissue as described herein for treating a skeletal muscle injury.

DETAILED DESCRIPTION OF THE PREFERRED EMBODIMENTS

Figure 1:
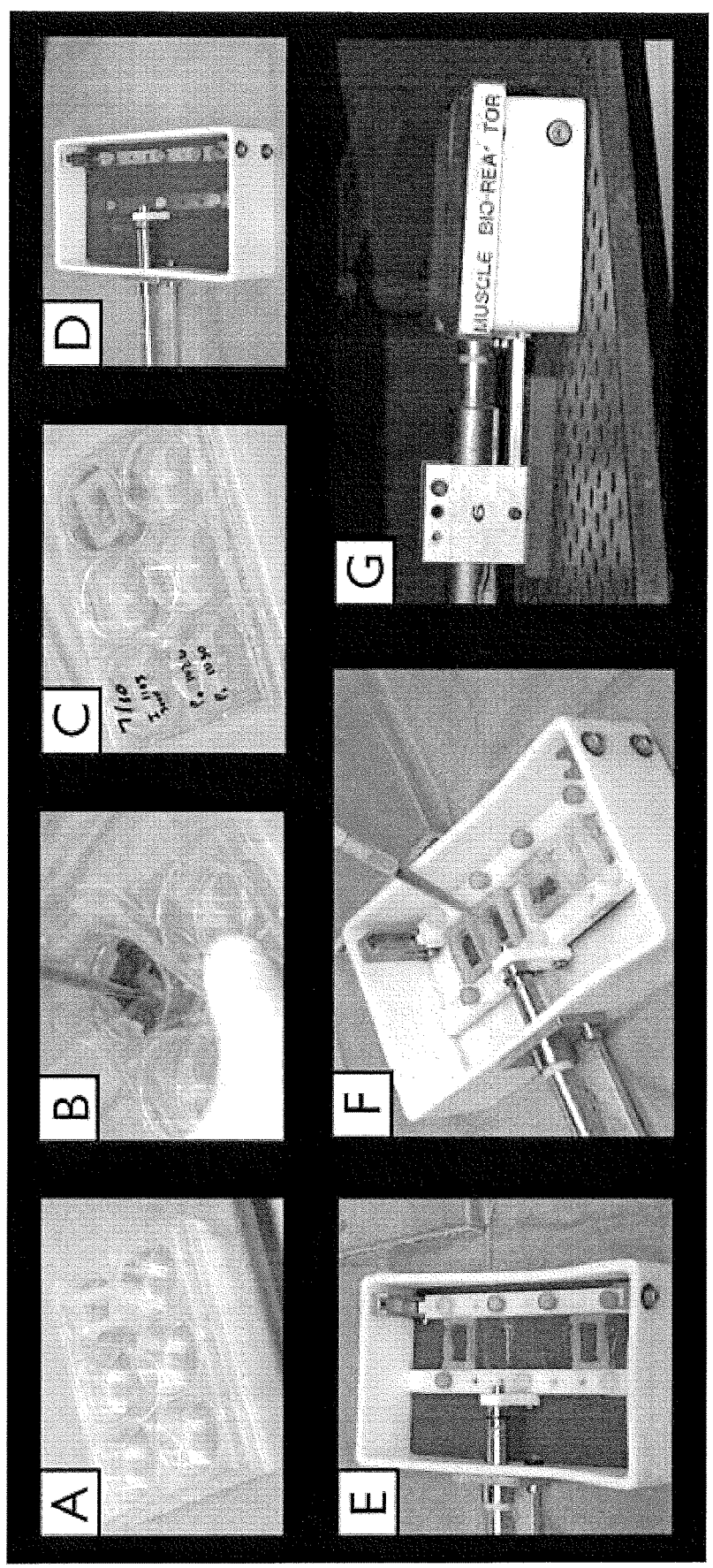
FIG. 1. Multiple seeding protocol of bladder acellular matrix (BAM) scaffold for TEMR. Scaffolds are initially seeded and incubated under static conditions for ten days (A, B, & C). The seeded scaffolds are then placed in the bioreactor for three days of pre-conditioning (D). Then, silicon molds are placed in the bioreactor (E), the myogenic media is removed from the bioreactor, and the scaffolds are seeded a second time (F). After 6 to 24 hours of static incubation, myogenic media is restored to the bioreactor wherein the scaffolds resume conditioning (G).

Provided herein and further described below are compositions and methods useful for producing functional muscle tissue in vitro for implantation in vivo. The disclosures of all United States patent references cited herein are hereby incorporated by reference to the extent they are consistent with the disclosure set forth herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Implant" refers to a product configured to repair, augment or replace (at least a portion of) a natural tissue of a subject (e.g., for veterinary or medical (human) applications). The term "implantable" means the device can be inserted, embedded, grafted or otherwise chronically attached or placed on or in a patient. Implants include a support having cells seeded thereon and/or subjected to bioconditioning according to some embodiments as described herein.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with or at risk for developing a disease (e.g., a musculoskeletal disease). Treating includes actions taken and actions refrained from being taken for the purpose of improving the condition of the patient (e.g., the relief of one or more symptoms), delay in the onset or progression of the disease, etc. In some embodiments, treating includes reconstructing skeletal muscle tissue (e.g., where such tissue has been damaged or lost by, e.g., injury or disease) by implanting an anisotropic scaffold (with or without muscle cells) into a subject in need thereof. Scaffolds may be implanted, e.g., at or adjacent to the site of injury, and/or at another site in the body of a subject that would impart a benefit to the subject, as would be appreciated by one of skill in the art.

"Isolated" as used herein signifies that the cells are placed into conditions other than their natural environment. Tissue or cells are "harvested" when initially isolated from a subject, e.g., a primary explant.

Muscle cells used to carry out the present invention are preferably mammalian muscle cells, including primate muscle cells, including but not limited to human, pig, goat, horse, mouse, rat, monkey, baboon, etc. In general, such cells are skeletal muscle cells. Muscle cells of other species, including birds, fish, reptiles, and amphibians, may also be used if so desired. In some embodiments the cells are precursor cells, or cells that are capable of differentiating into mature, multi-nucleates muscle cells, specifically skeletal muscle cells, under appropriate culture conditions and stimuli as described herein. Muscle precursor cells are known. See, e.g., U.S. Pat. No. 6,592,623.

"Skeletal muscle cells" include, but are not limited to, myoblasts, satellite cells and myotubes. "Myoblasts" are a type of muscle precursor cell, and are normally closely associated with myofibers during the course of their life cycle in the vertebrate organism. If the myofiber is injured, the myoblasts are capable of dividing and repopulating it. Typically, after muscle injuries myofibers become necrotic and am removed by macrophages (Hurme et al. (1991) Healing of skeletal muscle injury: an ultrastructural and immunohistochemical study, *Med. Sci Sports Exerc.* 23, 801-810). This induces proliferation and fusion of myoblasts to form multinucleated and elongated myotubes, which self-assemble to form a more organized structure, namely muscle fibers (Campion (1984) The muscle satellite cell: a review, *Int. Rev. Cytol.* 87, 225-251). "Myotubes" are elongated, multinucleated cells, normally formed by the fusion of myoblasts. Myotubes can develop into mature muscle fibers, which have peripherally-located nuclei and myofibrils in their cytoplasm (e.g., as found in mammals).

Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic or autologous (i.e., from the patient to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a bioscaffold graft) using standard biopsy techniques known in the art.

"Supports" on which muscle cells may be seeded and grown to produce cultured muscle tissue of the present invention include any suitable support. See, e.g., U.S. Pat. Nos. 6,998,418; 6,485,723; 6,206,931; 6,051,750; and 5,573,784. Supports may be formed from any suitable material, including but not limited to synthetic or natural polymers, other biopolymers, and combinations thereof. Examples include collagen supports or decellularized tissue supports (e.g., obtained from smooth muscle or skeletal muscle, such as a decellularized mammalian (e.g., porcine) bladder. If desired, an angiogenic compound such as VEGF can be seeded on or carried by the solid support to facilitate the formation of vascular cells or vasculature in the muscle tissue. The supports may be of any suitable configuration, but in some embodiments comprise, consist of, or consist essentially of a generally flat planar portion. The support may be of any suitable thickness, but in some embodiments are at least 20, 30, 50 or 100 uM thick, up to 600, 800, or 1000 uM thick, or more.

In some embodiments, supports may include a polymeric matrix (e.g., collagen, a hydrogel, etc.). In preferred embodiments of the present invention, supports have mechanical integrity sufficient to withstand the mechanical stimulation (e.g., cyclic loading) in a bioreactor to produce the desired skeletal muscle tissues. For example, in some embodiments supports are able to withstand the cell seeding and preferred bioreactor pre-conditioning protocols described herein for at least 5, 10, 15, 17 or 20 days or more.

Any suitable culture media can be used to grow cells in the present invention, including medias comprising serum and other undefined constituents, defined medias, or combinations thereof, such as RPMI, DMEM, etc.

The "primary culture" is the first culture to become established after seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express a certain protein or marker).

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other biological marker.

In some embodiments, cells are passaged once, twice, or three times. In still other embodiments, cells are passaged more than 3 times prior to use. In some embodiments, cells are passaged 0-1, 0-2 or 0-3 times. In some embodiments, cells are passaged 1-2, 1-3, or 1-4 or more times. In some embodiments, cells are passaged 2-3 or 2-4 or more times. In further embodiments, cells are passaged 5, 8, 10, 12 or 15 or more times. The number of passages used may be selected by, e.g., the relative production of one or more muscle cell proteins and/or markers of interest measured in the cell population after each passage.

Any suitable bioreactor device can be used to carry out the present invention, including those described in Yoo et al., US Patent Application Publication No. US2006/0239981 (Oct. 26, 2006) the disclosure of which is incorporated by reference herein in its entirety.

In some embodiments, a "mold" is provided which is configured to fit within the bioreactor and also designed to confine a cell suspension on top of and/or within one or more of the supports and/or supports seeded with cells. The mold may be made of a light-weight material (e.g., silicone, with a total weight, e.g., of 1-5 grams) and preferably does not significantly damage the underlying cellular structures when placed onto the support and/or support seeded with cells.

Multiple cell seeding protocols (with or without additional bioreactor preconditioning) are contemplated according to some embodiments. As an example, if each additional cell seeding is carried out during a time of between 2 and 4 days, the number of cell seedings according to some embodiments may be 2, 3, 4, 5, 6, 7, or 8 or more.

The length of stretching of the solid support according to some embodiments may be to a dimension at least 2, 5, 7 or 10% greater in length than the static position, and in some embodiments preferably not greater than 12, 15 or 20%, and the relaxing may comprise retracting the support to a dimension not greater in length than the static position. In some embodiments the "static position" may be intermediate between the stretched and relaxed position, and in such cases the relaxing may comprise retracting the support to a dimension at least 2, 5, 7 or 10% lesser in length than the static position.

The first time period, during which the stretching and relaxing occurs, may be of any suitable length, for example from 2 or 3 minutes up to 10, 20 or 30 minutes in duration or more. The step of cyclically stretching and relaxing is typically carried out at least two or three times during the first time period (e.g., from 2, 3 or 4 times, up to 10 or 20 times)

The second time period during which the support is maintained in a static position, may be of any suitable duration. In some embodiments the second time period is shorter than the first time period, and may be from 1 or 2 minutes in duration up to 10 or 20 minutes in duration. In other embodiments the second time period is longer than the first time period, and may be from 10 or 20 minutes in duration up to 40, 60 or 90 minutes in duration, or more. In some embodiments, the second time period is from 50 to 58 minutes in duration. In some embodiments, such as where the first time period contains comparatively long intervals between stretching and relaxing, the need for a second time period may be obviated altogether.

In one preferred embodiment, the support is cyclically stretched and relaxed during a first "active" time period to a dimension of 10% greater and lesser in length than the static dimension at a rate of 3 cycles per minute for a total of five minutes, followed by an approximately 25 minute or 55 minute "rest" second time period, continuously for 1 to 3 weeks of in vitro culture. In some embodiments, this improved protocol results in an increase in the number of multinucleated cells, thicker myotube width, better cellular alignment, etc., in the construct.

In some embodiments, this improved protocol of cyclic stretching and relaxing and/or multiple cell seeding may result in an increase in the number of multinucleated cells, thicker myotube width, better cellular alignment or orientation along an axis, etc., in the construct (by, e.g., 10, 20, 50, 80 or 100%).

"Oriented" cells typically have one (or more) axis of orientation (e.g., longitudinal axis), which may be in any desired direction within the region of interest. It will be appreciated that "orienting" as used herein may include partial or total orientation, so long as a sufficient increase in organization is achieved to produce the effect or benefit intended for the particular implementation of the methods described herein. For example, fibers and/or cells may be oriented along a longitudinal axis such that greater than 70, 80, 90, or 95% or more of the fibers and/or cells are at an angle of 50, 40, 30, 20, or 10 degrees or less from the reference axis in any direction.

In some embodiments, the construct is characterized by the expression of acetylcholine (ACh) receptors, and in some embodiments the ACh receptors are aggregated. In some embodiments, aggregated ACh receptors may include those which approximate the characteristic pretzel shape of a motor endplate in innervated mature fibers in vivo.

Skeletal muscle tissue produced as described herein may be used in vitro to examine the pharmacological or toxicological properties of compounds of interest (e.g., by adding the compound of interest to a culture medium in which the tissue is immersed, and examining the histological or mechanical properties of the tissue as compared to a control tissue).

Skeletal muscle tissue (with or without support) produced by the methods of the present invention is preferably "suturable" in that it has sufficient structural integrity to be surgically sutured or otherwise fastened at either end when implanted and thereafter develop tension upon contraction.

Skeletal muscle tissue produced as described herein may be used for the reconstruction of damaged tissue in a patient, e.g., a patient with a traumatic injury of an arm or leg. Such tissue may be utilized on the support (which is also implanted) or removed from the support and implanted into the subject. The skeletal muscle tissue may be implanted to "build" soft tissue (e.g., at the interface between an amputated limb and a prosthetic device) or to reconstruct (partially or totally) a damaged muscle (e.g., a muscle of the face, hand, foot, arm, leg, back or trunk). The cultured skeletal muscle tissue preferably has, in some embodiments, a size or volume of at least 1, 2, or 3 or more cubic centimeters (not counting the volume of the support if present), and/or a length of 1 cm to 50 cm, to provide sufficient tissue mass for implantation in a patient (e.g., in association with an existing muscle of the patient) and reconstruction of a skeletal muscle involved in, for example, movement of fingers.

For allogenic transplant into a patient, skeletal muscle as described herein may be matched or tissue-typed in accordance with known techniques, and/or the subject may be administered immune suppressive agents to combat tissue transplant rejection, also in accordance with known techniques.

The present invention is explained in greater detail in the following non-limiting Examples.

Example 1

Improvements to Muscle Bioreactor Conditioning to Form More Mature or "Native-Like" Skeletal Muscle Tissue Development of a methodology to perform multiple cell seeding on BAM scaffolds in the bioreactor. As depicted in FIG. 1a-d, our previous seeding model involved pipetting cells onto a bladder acellular matrix (BAM) scaffold under static conditions and then placing the muscle construct in the bioreactor for preconditioning.

In order to perform a second seeding on BAM scaffold that has already undergone a period of bioreactor preconditioning, a technique was developed to seed the scaffold while it remains in the bioreactor (FIG. 1e,f). The primary challenge to this approach is ensuring optimal scaffold coverage and ample opportunity for cellular adherence. Light-weight (~2 gram) silicon molds were constructed to create a custom seeding chamber within the bioreactor that constrains the muscle progenitor cell suspension to the top of each individual muscle construct. The placement of the silicon molds on the periphery of the muscle constructs does not appear to damage underlying cellular structures. Thus, the bioreactor has been adapted to accommodate cell seeding during preconditioning without the need to remove the scaffold (FIG. 1e,f).

Immunofluorescent microscopy was used to visualize myoblast and myotube cell morphological features on the BAM scaffold following static or bioreactor preconditioning at two different stretching frequencies (FIG. 2) in order to assess the enhanced bioreactor preconditioning on TEMR constructs in vitro.

Figure 3:
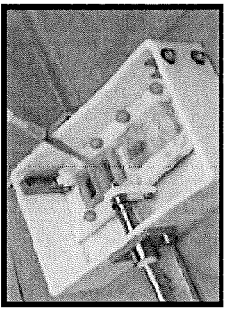
FIG. 3. Typical bioreactor preconditioning standard operating procedure (SOP).

Standard operating procedure (SOP). An SOP for an improved bioreactor preconditioning protocol that incorporates a second cell-seeding event is outlined in FIG. 3.

Discrimination between cells of different seedings. To be able to discriminate between the cells that were originally statically seeded prior to bioreactor preconditioning and those that have been subsequently seeded during bioreactor preconditioning, a red or green fluorescent cytoplasmic dye (CM-diI or CM-diO, respectively, INVITROGEN™) was applied to the cells that were subsequently incorporated onto the BAM scaffold in a second seeding event. In tandem, the retrieved constructs are stained with myogenic muscle markers (e.g., myoD & desmin) with a green fluorescent dye and nuclei with DAN (blue). This approach permits the simultaneous assessment of the presence of myoblasts as well as the formation/maturation of myotubes. In addition, the methodology permits evaluation of the contribution of each cellular seeding round to tissue formation for the TEMR construct.

Figure 4:
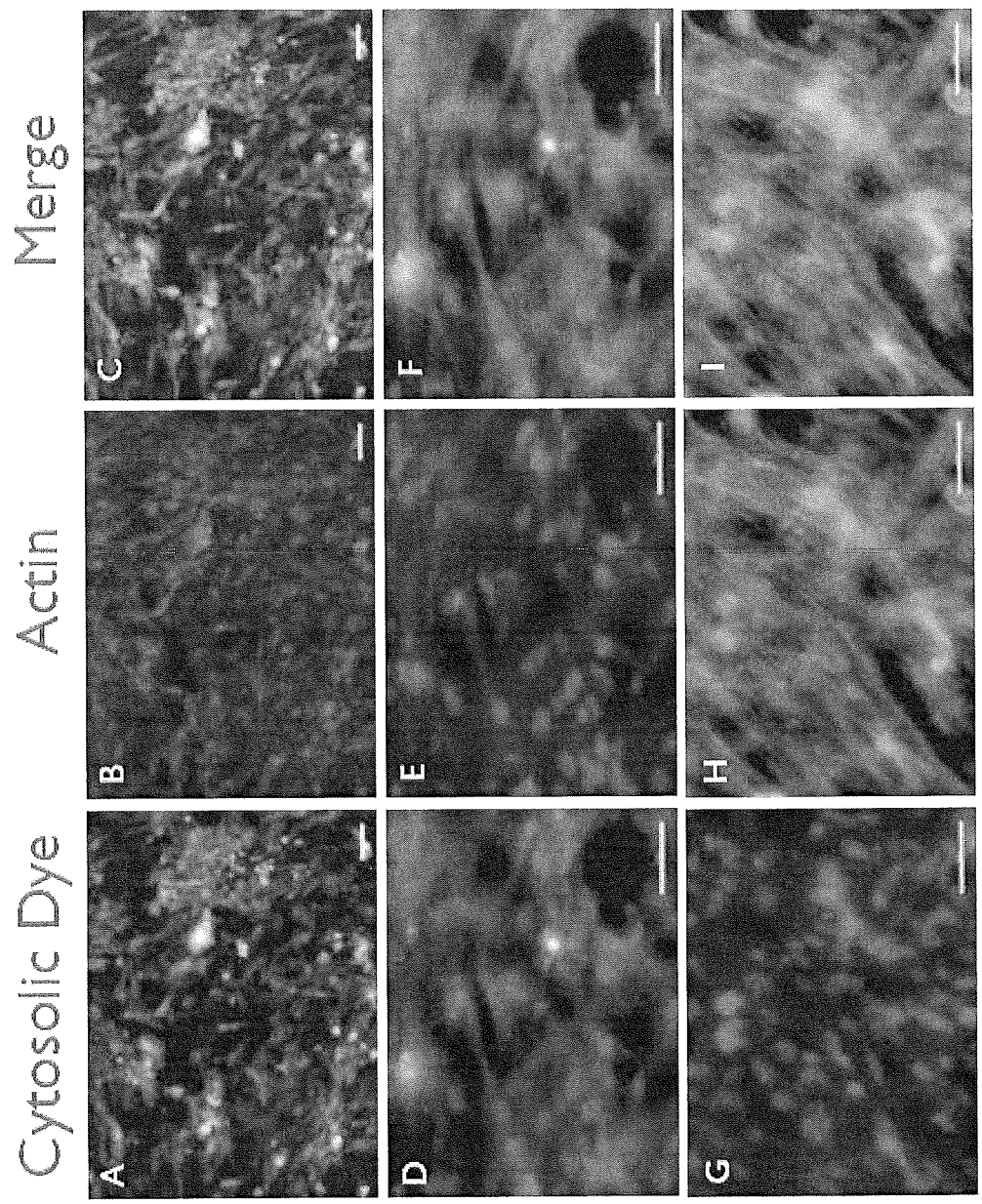
FIG. 4. Triple immunostaining method used for discriminatory visualization of the impact of bioreactor preconditioning and multiple/repeated cell seeding on the TEMR construct. Shown are representative images of the morphological characteristics observed following a 7d double-seeding bioreactor pre-conditioning protocol. The cytosol of cells in the second seeding event was loaded with either Cm-DiO or Cm-DiI fluorescent dye. Actin and nuclei of all cells were detected with phalloidin Alexa 594 or 488 and DAPI, respectively. During bioreactor preconditioning, constructs were stretched 3 times per minute for the first 5 minutes of every hour (A-F; 1×) or every half-hour (G-I; 2×) with a strain of 10%. Scale bar=50 μm.

FIG. 4 illustrates the application of this methodology to a BAM scaffold seeded in the bioreactor. Actin positive and cytosolic dye positive cells were visualized on the same BAM scaffold using the bioreactor-based seeding methodology illustrated in FIG. 3. Moreover, DAPI staining of nuclei is demonstrated in FIG. 4, indicating that employment of this triple staining technique may be used to discriminate between cells of the primary and secondary cell seedings.

Implementation of a multiple cell seeding protocol. Our previous seeding model involved pipetting cells onto BAM scaffolds under static conditions and then placing the muscle construct in the bioreactor for seven days of uniaxial stretching as follows: three times per minute for the first five minutes of each hour with 10% strain, continuously for seven days. To implement a second seeding event, we stopped the bioreactor three days into preconditioning and then performed a second seeding of the scaffold.

On day 1, BAM scaffolds with both a top and bottom silicon seeding chamber were initially wet with PBS and allowed to incubate at 37° C. for a minimum of 2 hours. For the initial seeding, MPCs of P1 were split and counted. The PBS was removed from the scaffolds and the cells, at a density of 1 million per $cm^2$ were pipetted onto the scaffold in a 'Z-like' fashion. The seeded scaffolds were placed into the incubator for approximately 30 minutes in which after a volume of 6 mL, enough to cover the scaffold, of seeding media was added into the dish. The scaffold was incubated overnight.

On day 2, more MPCs from tissue culture dishes were split and counted. Once the cells were ready for seeding, the scaffolds were removed from the incubator and the media was removed from their dish. Each scaffold was flipped to allow seeding of the second side. Cells were again pipetted in a 'Z-like' fashion onto the scaffold at the same density of 1 million per cm$^2$. The scaffolds were placed into the incubator at 37° C. for 30 minutes and then seeding media was added back into the dish enough to cover the top of the scaffold. The scaffolds were allowed to incubate for 2 more days with no disturbance.

The seeding media was removed from the dish and changed to differentiation media on day 5. Each dish received enough media to cover the top of the scaffold which was approximately 6 mL. This process of changing the media was repeated on day 8 and 10. At each of these times the media used was still differentiation media.

On day 11, the scaffolds were removed from their dishes and placed into a bioreactor for stretching. Bioreactor seeding media was used and total volume within the bioreactor was approximately 150 mL.

Day 15 includes the double seeding. MPCs were split from tissue culture plates and again counted. These cells were then centrifuged and resuspended in a DMEM serum free media at approximately 1 million cells per mL. CM-DiI or CM-DiO was added at a concentration of 1:2000 and the solution was allowed to incubate for 15 minutes at 37° C. The solution was centrifuged and resuspended in a PBS wash. The wash procedure was repeated a total of 3 times. After washing, the cells were finally resuspended in normal seeding media at density of 2 million cells per 1 mL. Also during this time, the scaffolds inside the bioreactor were being prepared for a second layer. The bioreactor was first removed from the incubator and the media removed. Silicone seeding chambers were fitted both below and above each scaffold while still inside the bioreactor to allow containment of the cells on top of each scaffold. The colored cells were pipetted on to each scaffold at a density of 1 million per cm$^2$ and allowed to sit undisturbed for 20 minutes. After this time approximately 75 mL of bioreactor seeding media was added to the bioreactor and it was placed inside the incubator for 6 hours. After this time, the silicone chambers were removed from the top and bottom of each scaffold and 75 more mL of bioreactor seeding media were added into the bioreactor. This procedure was not repeated for the following side; only one side of the scaffold received a second layer of cells.

| Time | Media |
|---|---|
| Day 1 to Day 4 | Seeding |
| Day 5 to Day 11 | Differentiation |
| Day 12 to Day 15 | Bioreactor Seeding |
| Day 15 | Seeding (for cells) |

The constructs were kept in static culture for 6-24 hours in order to maximize cellular adherence to the existing cell layer. Then, uniaxial stretching was resumed for the remainder of the preconditioning protocol (i.e., 2-3 days). Approximately 1 million cells per cm$^2$ were seeded onto the scaffold during the seeding event. FIG. 4 shows representative images collected following the SOP described in FIG. 3 for these experiments. Note that in FIG. 4, green (CmDiO) and red (CmDiI) cytosolic dyes, respectively, were loaded into cells prior to the second seeding only. A triple-staining immunofluorescence approach was used, in which the cytosol of cells used in the second round of seeding was visualized by loading of the cells with red or green dye, while the actin staining was visualized with phalloidin, and the nuclei of all cells on the scaffold were visualized via DAPI.

The major findings from these experiments were as follows:

Cells from the second seeding adhered to the scaffold or pre-existing layer of cells;

Some of the added cells fused with the existing cells;

The scaffold was comprised of aligned, multi-nucleated, actin-expressing cells; and At the end of bioreactor preconditioning, a multilayer construct was observed: That is, for example, 2, 3 or 5 layers of cells, up to 6 or 8 layers of cells, are observed in at least portions of the construct; while other portions of the construct may remain a monolayer of cells.

Interestingly, the observed colocalization of cytosolic dye with actin (FIG. 4 last column), suggests that a portion of the cells in the second-seeding are fusing with the pre-existing layer of cells, creating a population of elongated multi-nucleated myotubes. This is particularly advantageous for creation of TEMR constructs that better approximate mature muscle cell morphology and function, especially when one considers that muscle cell maturation and hypertrophy may be limited by the constraints of the nuclear domain.

Thus, increased fusing of the myoblasts into myotubes was observed with the double seeding protocol (and not just more cells). This is evidence that the cells are maturing more rapidly, proceeding down the pathway of satellite cell to myoblast to myotube, with the double seeding than without, making it more likely that they will form functional myofibers when implanted in vivo.

Figure 2:
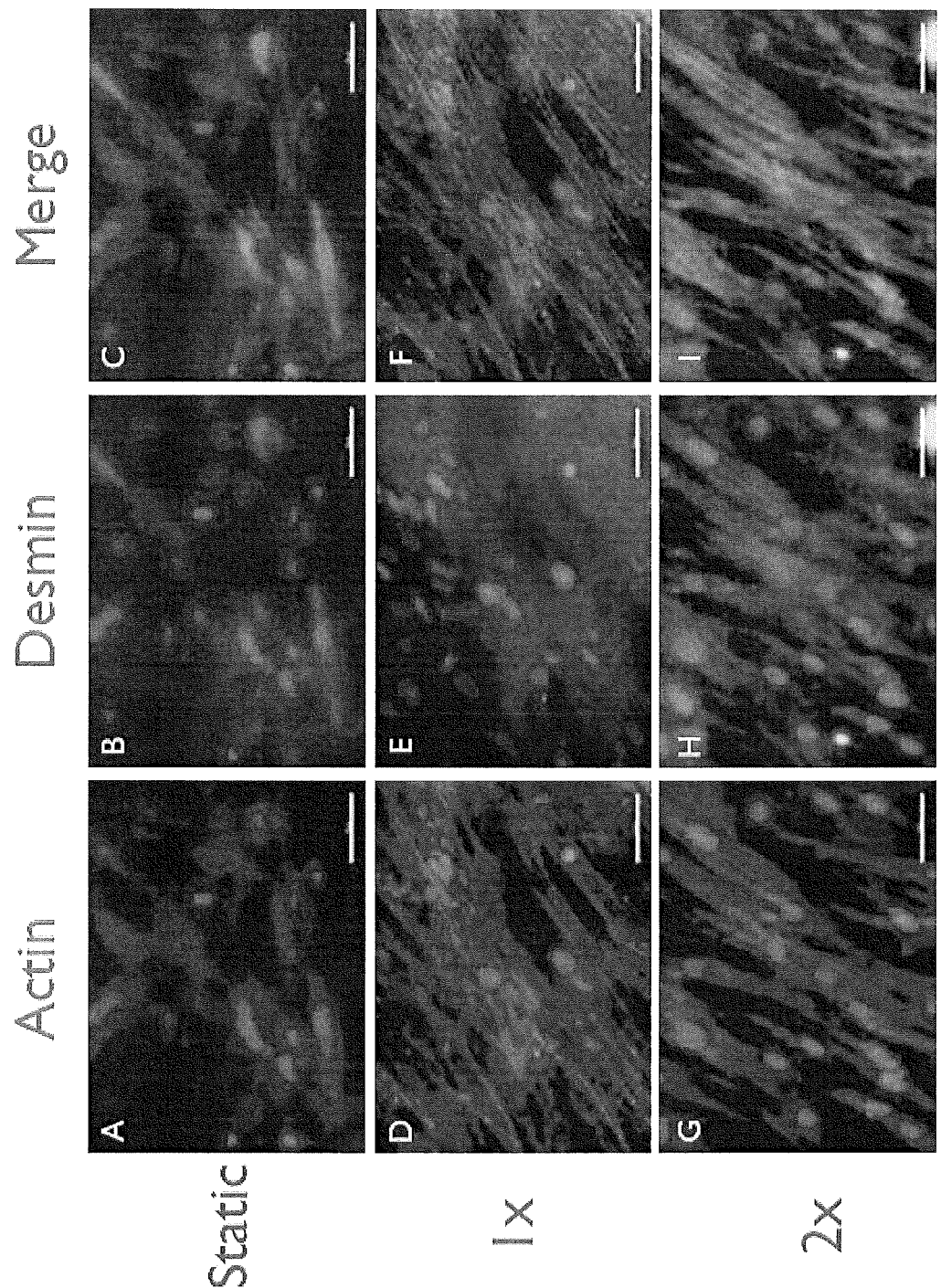
FIG. 2. Actin and desmin protein expression by TEMR constructs following static and bioreactor preconditioning at 10% strain and 3 stretch-relaxation cycles per minute for the first 5 minutes of every hour (1×) or half hour (2×). Actin and nuclei were detected with phalloidin Alex 594 and dapi, respectively, while desmin was detected with goat anti-rat polyclonal primary antibody (1:50) and rabbit anti-goat fluorescein secondary antibody (1:500). All images were captured at 400×; Scale bar=50 μm.
Figure 5:
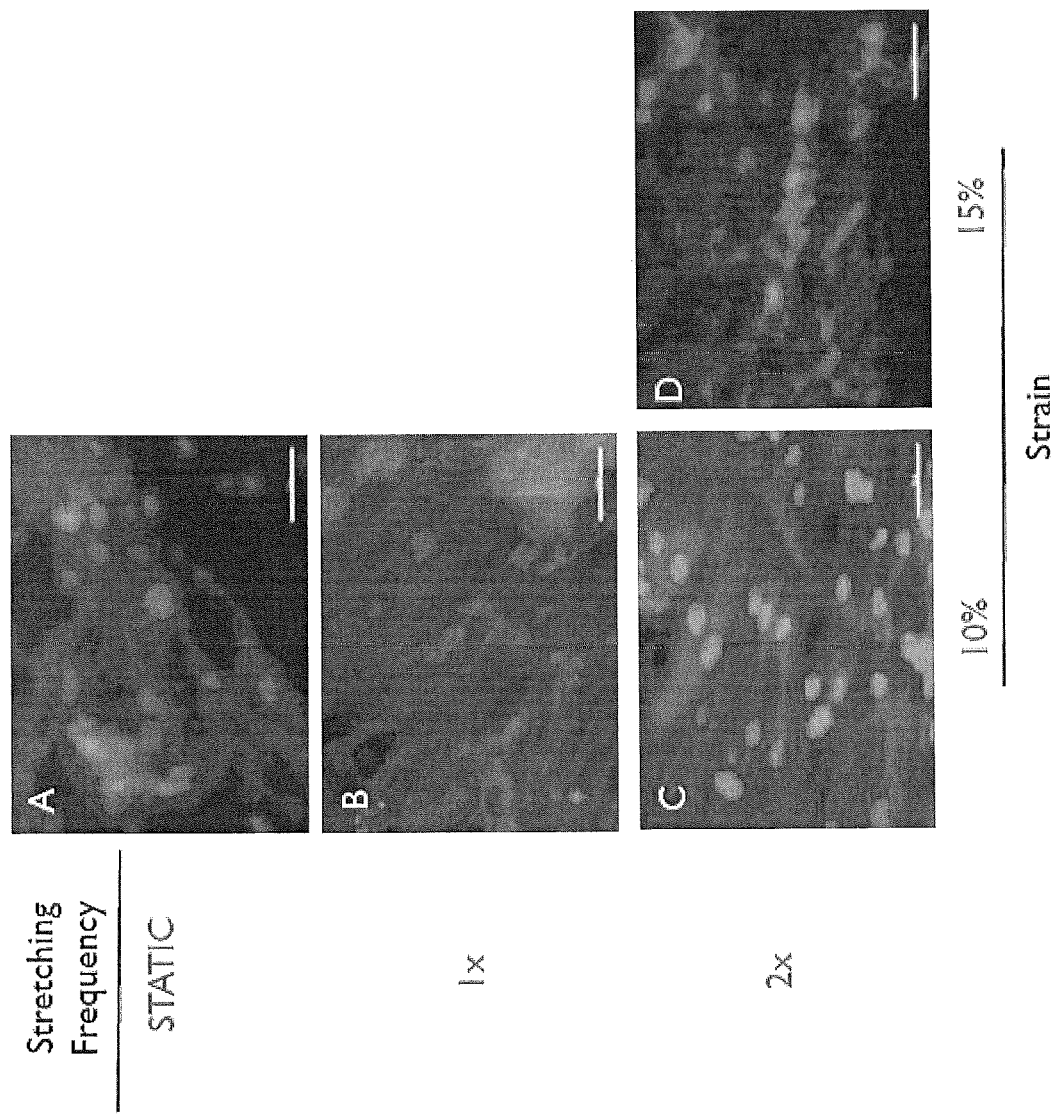
FIG. 5. Effect of varying mechanical properties on scaffold TEMR construct morphology. All constructs were either static (A) or underwent uniaxial stretching in the bioreactor (B-D) for seven days. Bioreactor— preconditioned scaffolds were stretched three times per minute for the first five minutes of each hour (1×; B) or half hour (2×; C & D) with 10% (B & C) or 15% (D) strain. Immunofluorescence images are at 400× magnification with actin and nuclei stained phalloidin and dapi, respectively. Scale bar=50 um.
Figure 6:
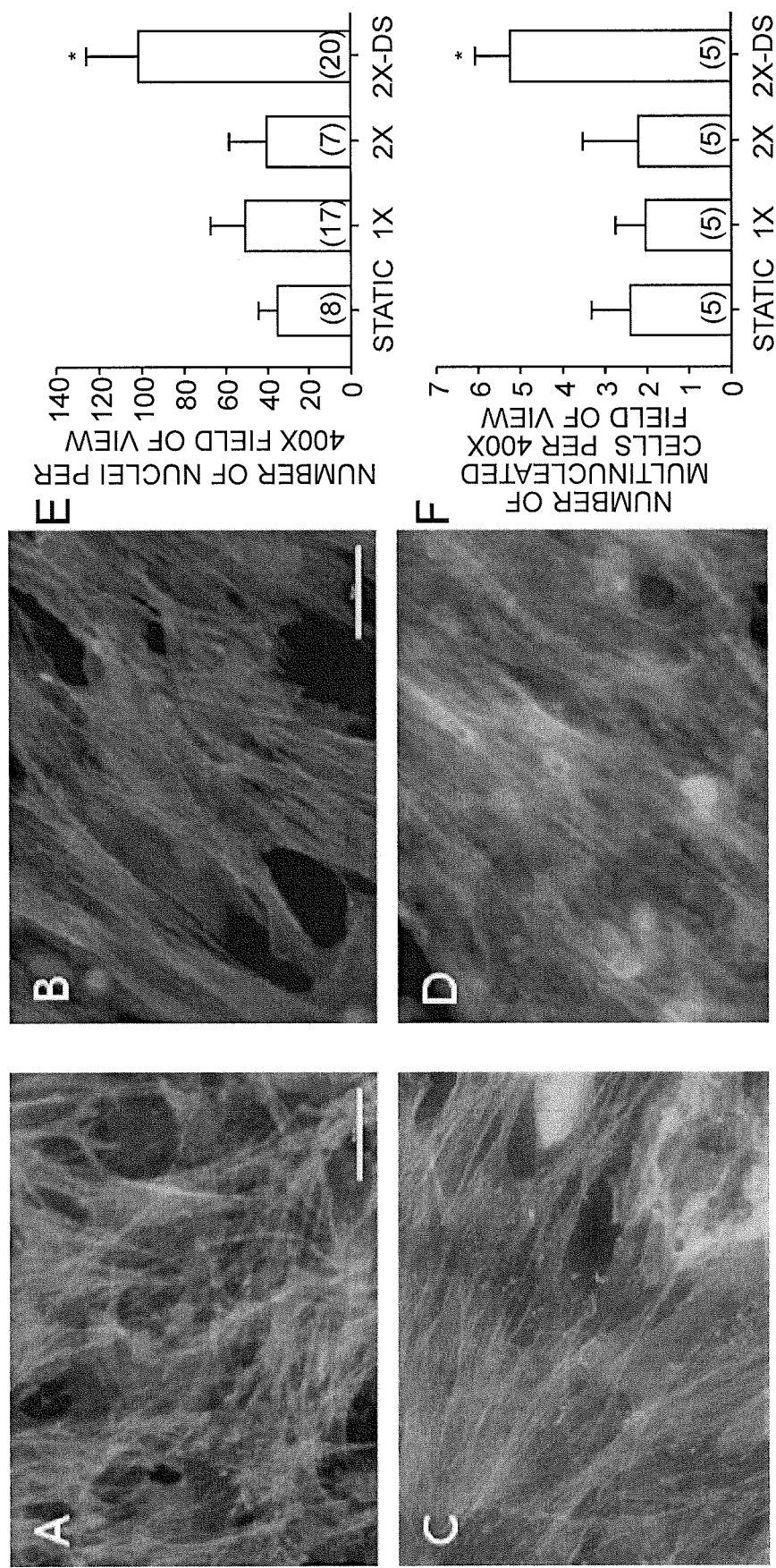
FIG. 6. Tissue engineered skeletal muscle construct morphology following bioreactor preconditioning. Constructs either remained static for the duration of bioreactor preconditioning protocol (A), or were conditioned with different bioreactor protocols (B-D). Scaffolds were uniaxially stretched 3 times per minute for the first 5 minutes of every hour (B; 1×) or half hour (C; 2×) for one week. Additionally, 2× constructs underwent a second cell seeding, while in the bioreactor, three days into the one-week protocol and then resumed stretching following a 6 hour static interval (D; 2×-DS). Constructs are stained for actin (phalloidin) and nuclei (dapi). All images are at 400× magnification. The number of nuclei and number of multinucleated cells were counted from the number of 400× images listed in parentheses that were derived from at least three different constructs. The number of nuclei were counted using ImageJ software. The number of multinucleated cells were determined by a blinded researcher. *Indicates that 2×-DS constructs had significantly more nuclei (E) and multinucleated cells (F) than all other construct types (p<0.01). Values listed are means f SD.

Optimization of bioreactor preconditioning mechanical parameters (i.e., mechanical stretch). In addition to developing and implementing a bioreactor preconditioning protocol that permits multiple/repeated cellular seeding, we also characterized the morphology of TEMR constructs subjected to bioreactor preconditioning using distinct stretching protocols, by varying mechanical parameters. For these experiments, all TEMR constructs were kept in static culture for 10 days following initial cell seeding (FIG. 2). Based on these data, it appears that bioreactor preconditioning at a strain of 10-15% and a frequency of 3 times per minute for the first 5 minutes of every hour to half hour improves cell density, differentiation (e.g., multinucleated cells), alignment, and morphology compared to constructs cultured statically for the same culture duration (See FIG. 5A for representative static culture image compared to bioreactor preconditioned constructs FIGS. 5B & 5C). Additionally, increasing the stretching frequency and applying a double seeding increases the number of multinucleated cells on the scaffold (DS protocol) (FIG. 6).

Figure 7:
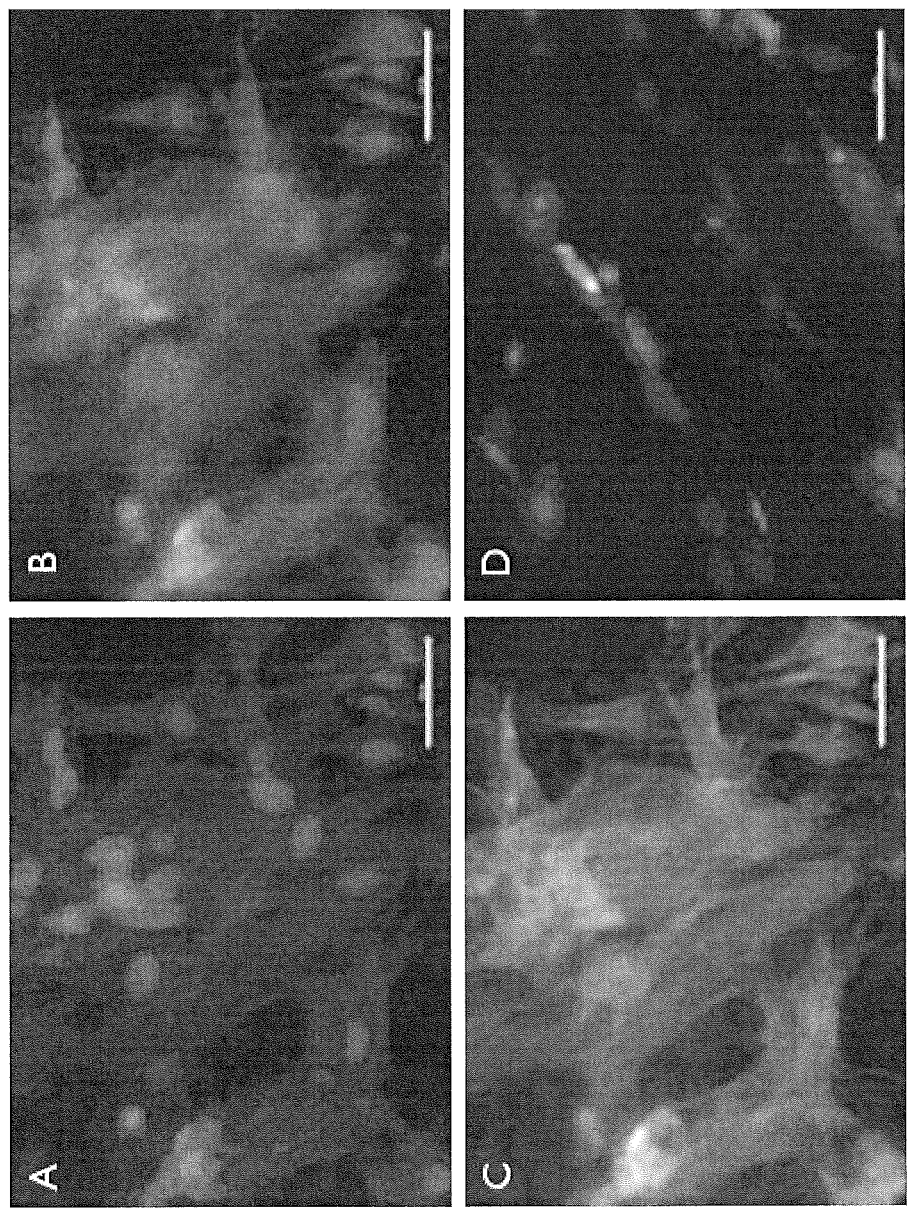
FIG. 7. Acetylcholine receptor expression in TEMR constructs. For images A-C, actin, acetylcholine receptors, and nuclei were detected with phalloidin Alexa 594, a-bungarotoxin Alexa 488 and DAPI, respectively. Image C represents the merger of images A & B. For image D, desmin was detected with a combination of goat antirat polyclonal primary antibody (1:50) and rabbit anti-goat rhodamine secondary antibody (1:500), and acetylcholine receptors and nuclei were stained with a-bungarotoxin Alexa 488 and DAPI, respectively. All images were captured at 400× magnification; Scale bar=50 μm.

Expression of acetylcholine receptors. During the characterization of TEMR construct morphology following bioreactor preconditioning, we discovered that multinucleated cells of TEMR constructs expressed acetylcholine (ACh) receptors and, in rare cases, exhibited aggregation of these receptors (FIG. 7). Interestingly, the aggregation of ACh receptors in one construct is beginning to exhibit the characteristic pretzel shape of a motor endplate in mature fibers (FIG. 7D). These novel findings are encouraging for the development of TEMR constructs that produce clinically relevant force, as innervation of implanted TEMR constructs is crucial for functional restoration of traumatically injured muscle tissue, and we now know that these cells 1) express ACh receptors and 2) have the capacity to develop a motor endplate.

Example 2

Rodent Muscle Injury Model, Demonstrating that Improved Bioreactor Protocols In Vitro Lead to Accelerated Maturation and Improved Functional Outcomes In Vivo Experimental Design. Different strategies of culturing a mixed population of muscle precursor cells (MPCs) on bladder acellular matrix (BAM) collagen scaffolds were used to create tissue engineered muscle repair (TEMR) constructs with distinctly different morphological and protein expression characteristics. Briefly, one group of constructs experienced a short cellular proliferation and growth period, a second group experienced a prolonged cellular maturation period, and a third group was designed to reflect both of these conditions by applying a second population of MPCs to an underlying layer of maturing cells three days before implantation. Based on the culture and seeding conditions used to generate each construct type, the experimental groups are referred to as: Proliferation, Differentiation, and Mixed, respectively. TEMR constructs derived from all three in vitro procedures were implanted at the site of a freshly made volumetric muscle loss injury in the latissimus dorsi muscle of nude mice. One and two months after injury and implantation, contralateral control, non-repaired, and TEMR construct-repaired (three groups) LD muscles were retrieved. Subsequent assessments of functional capacity and tissue repair and regeneration were conducted to compare the therapeutic benefits of these distinct TEMR constructs.

Animals. Male Lewis rats (3-4 weeks) and female athymic nude/nude mice (8-10 weeks) were used for muscle precursor cell donors or for in vivo studies of VML injury repair, respectively. Rodents were purchased from commercial vendors (Harlan and Jackson Laboratories). All animal procedures were approved by the Wake Forest University IACUC and are in accordance with animal use guideline set by the American Physiological Society.

Experimental Methods

Precursor cell isolation. Tibialis anterior and soleus muscles from 3 to 4 week old male Lewis rats were harvested for primary cell culture using methodology described previously. (Machingal) Briefly, skeletal muscles were digested in 0.2% Collagenase (Worthington biochemicals, Lakewood, N.J.) solution prepared in low glucose Dulbecco's Modified Eagle Medium (DMEM) (Hyclone, Logan, Utah) for two hours 37° C. Muscle tissue fragments were plated onto tissue culture dishes coated with MATRIGEL®, (BD Biosciences, Bedford, Mass.) in myogenic medium containing: DMEM high glucose supplemented with 20% Fetal Bovine Serum (FBS), 10% Horse Serum, 1% Chicken Embryo Extract and 1% Antibiotic/Antimycotic (Hyclone; Logan, Utah). Cells were passaged at ~75% confluence, cultured in DMEM low glucose supplemented with 15% Fetal Bovine Serum (FBS) and 1% Antibiotic/Antimycotic and used for seeding at the second passage.

BAM preparation. BAM scaffolds were prepared from porcine urinary bladder in accordance with known techniques. (Machingal et al., 2011) Briefly, the bladder was washed and trimmed to obtain the lamina propria, which was placed in 0.05% Trypsin (Hyclone, Logan, Utah) for one hour at 37° C. The bladder was then transferred to DMEM solution supplemented with 10% FBS and 1% Antibiotic/Antimycotic and kept overnight at 4° C. The preparation was then washed in a solution containing 1% TRITON™ X (Sigma-Aldrich, St Louis, Mo.) and 0.1% Ammonium hydroxide (Fisher Scientific, Fairlown, N.J.) in de-ionized water for 4 days at 4° C. Finally, the bladder was then washed in de-ionized water for 3 days at 4° C. The absence of cellular elements and preservation of structural components was confirmed by histological assessments. The decellularized scaffold was further dissected to obtain a scaffold with of 0.2-0.4 mm thickness; dimensions suitable for implantation in the surgically created mouse LD defect. The prepared acellular matrix was then cut into strips of 3 cm×2 cm size and placed onto a custom designed seeding chamber made of silicon (McMaster Carr, Cleveland, Ohio). Scaffolds and silicon seeding chambers were then individually placed in six well culture dishes and sterilized by ethylene oxide (FIG. 9F).

TEMR construct preparation. Sterilized scaffolds in custom-made silicon seeding chambers were kept immersed in a seeding media consisting of DMEM solution supplemented with 15% FBS and 1% antibiotic/antimycotic media for at least 12 hours at 37° C. prior to seeding. MPC's (Passage 2) were then seeded at a concentration of 1 million cells per $cm^2$, and after 12 hours, the seeding chamber was flipped and a concentration of 1 million cells per $cm^2$ was seeded on the other side. After a total of three days in seeding media, the "Proliferation" group was collected for either in vitro analyses or implantation.

Constructs belonging to the "Differentiation" or the "Mixed" groups were then immersed in differentiation media (F12 DMEM, 2% horse serum, 1% AA), wherein the cells were cultured for an additional 7 days. After a total of 10 days of static culture, the cell-seeded scaffolds (i.e., tissue engineered skeletal muscle or TE-MR) were then placed in a bioreactor system, in accordance with known techniques. The bioreactor system consisted of a computer-controlled linear motor powered actuator that directed cyclic unidirectional stretch and relaxation. To permit application of the cyclic stretch protocol, one end of the TE-MR construct was attached to a stationary bar, while the other end was connected to a movable bar attached to the actuator. TEMR constructs were subjected to ~10% strain, 3 times per minute for the first five minutes of every hour, for five to seven days in accordance with known techniques. Constructs that underwent the full static and dynamic differentiation protocols comprised the "Differentiation" group. Additionally, a third set of constructs called the "Mixed" group was created by stopping uniaxial stretching midway through preconditioning (i.e., 2-3 days), applying a second set of MPCs ($1^{st}$ or $2^{nd}$ passage) at a density of 1 million cells per $cm^2$ to only one side of the construct, allowing for static cellular adherence over a 6 to 12 hour period, and then proceeding with uniaxial stretching (same conditions) for two days. During the entire cell culture process, both cell seeded surfaces (i.e., top and bottom of the same BAM scaffold) were fully immersed in media, the constructs were continuously aerated with 95% air-5% $CO_2$ at 37° C. in an incubator and media was changed every 3 days.

Immunocytochemistry and Analysis. MPCs (P2) were seeded either on uncoated chamber slides or BAM scaffolds at a density of 1 million cells per $cm^2$. Whole mount staining was performed by fixing the cells in 2% formalin, washing in PBS-glycine (10 mM), permeabilized with 0.5% TRITON™, and then washed again in PBS-glycine. Cells were then blocked in 3% (w/v) non-fat dried milk in PBS for 30 minutes at room temperature prior to incubation with primary antibodies (1:50 in PBS) raised in mouse against desmin (Santa Cruz, -7955), myoD (Hybridoma Bank), and Pax7 (Hybridoma Bank) or phalloidin-Alexa Fluor 488 or 594 conjugated (1:50, Invitrogen) for one hour. Following washing in PBS, cells were incubated in Texas Red-conjugated anti-mouse IgG (Vector; 1:100) secondary antibody for thirty minutes and were then washed again in PBS. Probed specimens were then coverslipped with PRO-LONG® Gold including DAPI (invitrogen-P36931).

To determine the percentage of P2 MPCs expressing pax7, myoD, or desmin on chamberslides, the total number of nuclei and positively labeled nuclei were counted in at least 12 high-powered field (400×) images from at least two different chamber slides, resulting in over 800 nuclei counted per protein marker. The percentage of positive cells are expressed as total positive cells of total cells counted.

To assess the cellular morphology and number nuclei on BAM scaffolds, the number of nuclei and number of multinucleated cells were counted from 400× images derived from at least three different constructs each. The number of nuclei were counted using ImageJ software. The number of multinucleated cells was determined by a researcher who was blinded to the experimental conditions. Multinucleated cells were defined as a structure in which two or more nuclei were associated with the same set of actin stress fibers.

BAM Scaffold Mechanical testing. Uniaxial tensile mechanical testing was performed using an INSTRON® 55401. Prepared sterilized BAM scaffolds were incubated at 37° C. in DMEM for ~24 hours prior to testing. BAM samples were uniformly prepared with a width of 3.75 mm using a standard steal press. Samples were kept hydrated during preparation and testing. Pretension was set to 0.2 N. Samples were tested to failure using a strain rate of 0.5 mm/s. Young's modulus was calculated from the slope of the linear portion of the stress-strain curve using.

Surgical creation of VML injury and TEMR construct Implantation. VML injury was created by surgically creating a critical size defect of the LD muscle in anesthetized (isoflurane) nu/nu mice using similar methodology to our previous report. (Machingal) A longitudinal incision was made along the midline of the back. The trapezius muscle that covers the LD muscle was lifted to expose the LD muscle without removing the tendon inserted at the humerus. Suture markers were then placed on the LD muscle demarking the superior half of the spinal fascia and the medial half of the of the muscle head at the humerus. The medial half of the muscle was then excised using a fine scissor. Using this methodology, a defect weighing ~18 mg was excised from the LD muscle. The injured LD muscle was then either left without further treatment or an ~3×1 cm TEMR construct was sutured (Vicryl 6-0) to the site of injury. In all cases, the fascia and skin were then sutured closed and the animals were allowed to recover from anesthesia.

In vitro functional assessment. Whole LD muscles were dissected free and studied in vitro using a DMT organ bath system (DMT Model 750TOBS) and similar methodology in accordance with known techniques. LD muscles were mounted in an organ bath chamber containing a Krebs-Ringer bicarbonate buffer (pH 7.4) with (in mM) 121.0 NaCl, 5.0 KCl, 0.5 MgCl$_2$, 1.8 CaCl$_2$, 24.0 NaHCO$_3$, 0.4 NaH$_2$PO$_4$, and 5.5 glucose (the buffer was equilibrated with 95% O$_2$-5% CO$_2$ gas). The distal tendon was attached by silk suture and cyanoacrylate adhesive to a fixed support, and the proximal tendon was attached to the lever arm of a force transducer (DMT 750TOBS). The muscle was positioned between custom-made platinum electrodes. Direct muscle electrical stimulation (0.2 ms pulse at 30V) was applied across the LD muscle using a Grass S88 stimulator (Grass Instruments, Quincy, Mass.). Real time display and recording of all force measurements were performed on a PC with POWERLAB®/8sp (ADInstruments, Colorado Springs, Col.).

Once the LD muscles were mounted in the organ bath, the muscles were allowed to equilibrate for 5 minutes prior to determining optimal physiological muscle length ($L_O$) via a series of twitch contractions. Maximal force as a function of stimulation frequency (1-200 Hz) was measured at 35° C. during isometric contractions (750 ms trains of 0.2 ms pulses), with 2 min between contractions. Absolute forces (mN) as a function of stimulation frequency were fit with the following equation:

$$f(x) = \min + (\max - \min)/[1 + (x/EC50)^{-n}]. \quad \text{Eqn 1.}$$

Where x is the stimulation frequency, min and max are the smallest (i.e., twitch; $P_t$) and largest (i.e., peak tetanic; $P_O$) respective forces estimated. EC50 is the stimulation frequency at which half the amplitude of force (max−min) is reached and n is the coefficient describing the slope of the steep portion of the curve. Measured $P_t$ and $P_O$ and maximal tetanic force at 80 Hz ($P_{80Hz}$), an index of measured force at approximately EC50, were compared during statistical analyses.

Additionally, $P_O$ was normalized to an approximate physiological cross-sectional area (PCSA), which was calculated using the following equation:

$$\text{PCSA} = \{\text{wet wt(g)}/[\text{muscle density(g/cm}^3)*(\text{muscle length(cm))}]\} \quad \text{Eqn 2.}$$

Where muscle density is 1.06 g/cm$^3$. For a subset of muscles, following force-frequency testing a caffeine contracture force assessment was performed. For these studies, a maximal caffeine contracture response was elicited by exposing the muscle to 50 mM caffeine during twitch contractions at a rate of 0.2 Hz. This concentration of caffeine was chosen because concentrations in the mM range have been previously shown to maximally stimulate whole uninjured and injured rodent skeletal muscle. During this testing, resting tension of the muscle increases until active force and resting tension are indistinguishable and then the response plateaus. Peak caffeine contracture force was defined as the tension measured at this steady-state response.

Western Blotting. TEMR constructs collected before implantation were rinsed with PBS and then minced and incubated for 30 minutes in 200 µL of NP-40 lysis buffer with a protease inhibitor cocktail (PIC: 40 µL/mL; Sigma P8340) resting on ice. Following incubation, the lysis suspension was centrifuged at 7000 g for 10 minutes at 4° C. The supernatant was stored at −80° C. until further use.

Uninjured, injured, and injured and repaired whole LD muscles were snap frozen in liquid nitrogen and stored at −80° C. LD muscles were thawed on ice, minced in 800 µL of homogenization buffer A (250 mM sucrose, 100 mM KCl, 20 mM MOPs, 5 mM EDTA, pH 6.8)+PIC and then homogenized using a PowerGen 125 tissue homogenizer (Fisher Scientific) to make a whole muscle homogenate. A portion (675 µL) of the whole homogenate was then further processed to extract the myofibrillar fraction in accordance with known techniques. Whole homogenates were centrifuged at 10,000 g for 10 min at 4° C. The pellet was then resuspended in a 800 µL of wash buffer (175 mM KCl, 2 mM EDTA, 0.5% TritonX100, 20 mM MOPs, pH 6.8) prior to undergoing a second centrifugation at 10,0000 for 10 min at 4° C. The pellet was then resuspended in 500 µL of homogenization buffer C (150 mM KCl, 20 mM MOPs, pH 7.0) with protease inhibitor cocktail. Whole muscle and myofibrillar fraction homogenates were stored at 80° C. until use. Protein concentration in homogenates was determined using a Bradford assay (Biorad Protein Assay Dye Reagent—500-0006).

TEMR construct, whole muscle, and myofibrillar homogenates were diluted in lamealli sample buffer with β-mercaptoethanol and then placed in boiling water for 3 minutes. From each respective homogenate type 60, 25, and 15 μg of protein per sample was loaded into 7, 7, and 10% polyacrylamide gels and separated using SDS-PAGE. The separated proteins were then transferred to a PVDF membrane (Millipore, IMMOBILON® membrane 0.45 μm pore), which was blocked overnight at 4° C. in 5% (w/v) non-fat dried milk suspended in PBS-TWEEN®. For the TEMR construct protein expression characterization, membranes were probed with mouse-derived anti-desmin (Sigma D1033; 1:200), pax7 (Hybridoma Bank; 1:25), myosin (Hybridoma Bank MF20; 1:100), embryonic myosin heavy chain (Hybridoma Bank F1.652; 1:100), and gapdh (Millipore MAB374; 1:1000) in PBS-T for three hours at room temperature. For the whole LD muscle homogenate analysis, membranes were probed with rabbit-derived anti-junctophilin1 (Invitrogen 40-5100; 1:20,000) and mouse-derived anti-desmin (Sigma D1033; 1:200), pax7 (Hybridoma Bank; 1:50), and gapdh (Millipore MAB374; 1:1000) in PBS-T for two hours at room temperature. For the myofibrillar fraction homogenate analysis, membranes were probed with mouse-derived anti-myosin (Hybridoma Bank MF20; 1:500) and gaph (Millipore MAB374; 1:1000). Following washing in PBS-T, membranes were incubated in anti-mouse or rabbit HRP conjugated secondary antibodies (Cell Signal 7074 & 7076) in PBS-T (1:20,000) for two hours at room temperature. Membranes were washed in PBS-T before detection using a SUPERSIGNAL® West Femto Chemiluminescent Substrate kit (Thermo Scientific 34096) and FUJIFILM® Intelligent Dark Box (LAS-3000). Optical density of the blot was determined using ImageJ. All protein markers were normalized to the optical density of gapdh.

Histology and Immunohistochemistry. LD muscles from all experimental groups were fixed in 10% neutral buffered formalin and stored in 60% ethanol. All samples were processed (ASP300S, Leica Microsystems, Bannockburn, Ill.) and then embedded in paraffin (EG1160, Leica Microsystems, Bannockburn, Ill.). Seven μM thick serial sections were Cut from the paraffin embedded blocks and Masson's Trichrome staining and immunohistochemical staining was performed using standard procedures. Immunohistochemical staining was performed using antibodies to detect desmin (M0760, 1:75, Dako, Carpinteria, Calif.), junctophilin 1 (Jp1; Invitrogen 40-5100, 1:120), myosin (MF-20, 1:10), ryanodine receptor 1 (RyR1; 34 C, 1:10), and Pax7 (1:150). MF-20, RyR1, and Pax7 antibodies were acquired from Developmental Studies Hybridoma Bank, Iowa City, Iowa. Biotinylated anti-mouse IgG (MKB-2225, 1:250, Vector Laboratories Inc, Burlingame, Calif.) and anti-rabbit (BA-1000, 1:500, Vector Laboratories Inc, Burlingame, Calif.) secondary antibodies were used to detect mouse (desmin, MF-20, RyR1, Pax7) and rabbit (Jp1) primary antibodies. The sections were next treated with Avidin Biotin Complex Reagent (PK-7100, Vector Laboratories Inc, Burlingame, Calif.) and then visualized using a NOVARED® substrate kit (SK-4800, Vector Laboratories Inc, Burlingame, Calif.). Finally, the sections were counterstained using Gill's Hematoxylin (GHS280, Sigma-Aldrich, St. Louis, Mo.). Tissue sections without primary antibody were used as negative controls. Images were captured and digitized (DM4000B Leica Upright Microscope, Leica Microsystems, Bannockburn, Ill.) at varying magnifications.

Results

BAM Characterization. BAM scaffolds were prepared and seeded with MPCs as described previously. (Machingal) Acellularity of the BAM scaffolds was confirmed by looking for the presence of nuclei or cellular protein (FIG. 1). In both cases, cellular presence was not observed, as nuclei were not present upon dapi whole mount staining and no cellular protein was detected via Bradford assay or visually on PVDF membranes following SDS-PAGE. Tensile mechanical properties of BAM scaffolds prior to seeding with MPCs were characterized. BAM scaffolds exhibited a Young's Modulus of 7.62±1.25 MPa with a stress of 1.13±0.21 MPa at failure, which are similar values to other previously described acellular collagen matrices.

Figure 8:
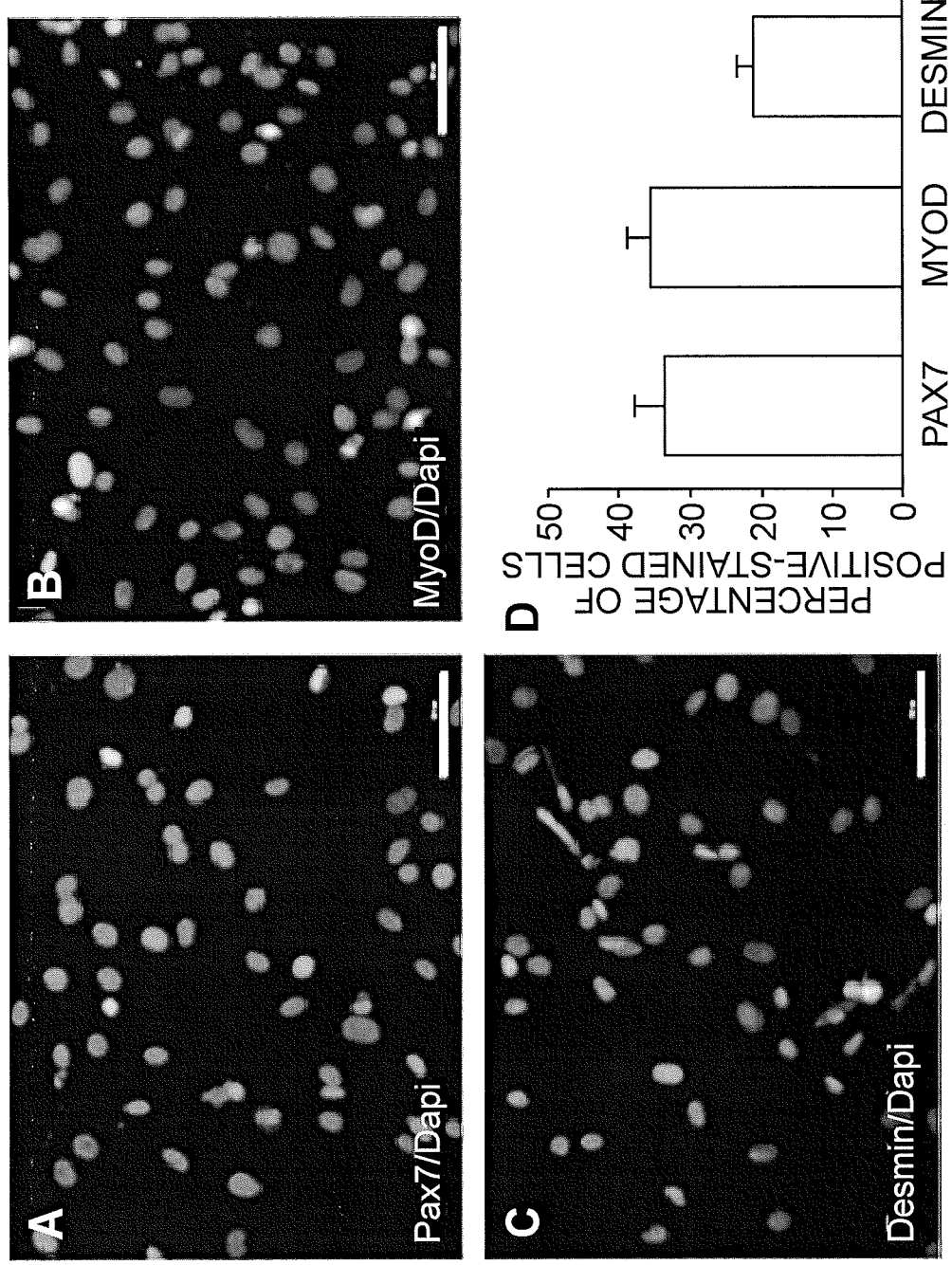
FIG. 8. Rat muscle progenitor cell (MPC) protein expression and bladder acellular matrix scaffold characteristics. MPCs from primary culture were passaged once, seeded on non-coated chamber slides, and then cultured for 1 day in proliferation media (See methods described in Example 3). Per protein marker, the total number of nuclei and positively stained nuclei (A-C) were counted in at least 12 high-powered field (400×) images from at least two different chamber slides. Over 800 nuclei were counted for each protein marker with the number of positive cells expressed as percentage of total nuclei (D). Bladder acellular matrix collagen scaffolds were cut to ~3×1 sheet prior to implantation (E; scaffold was rehydrated in media for picture contrast). Young's modulus was determined for seven sterilized and rehydrated scaffolds (F). Scaffolds were confirmed to be decellularized via the absence of a protein signature (Ponceau) or specifically Gapdh (blot; G), as well as the absence of nuclei (dapi; H). Protein expression (G) as well as nuclear staining via dapi (I) is demonstrated on BAM scaffold following the addition of MPCs.
Figure 8:
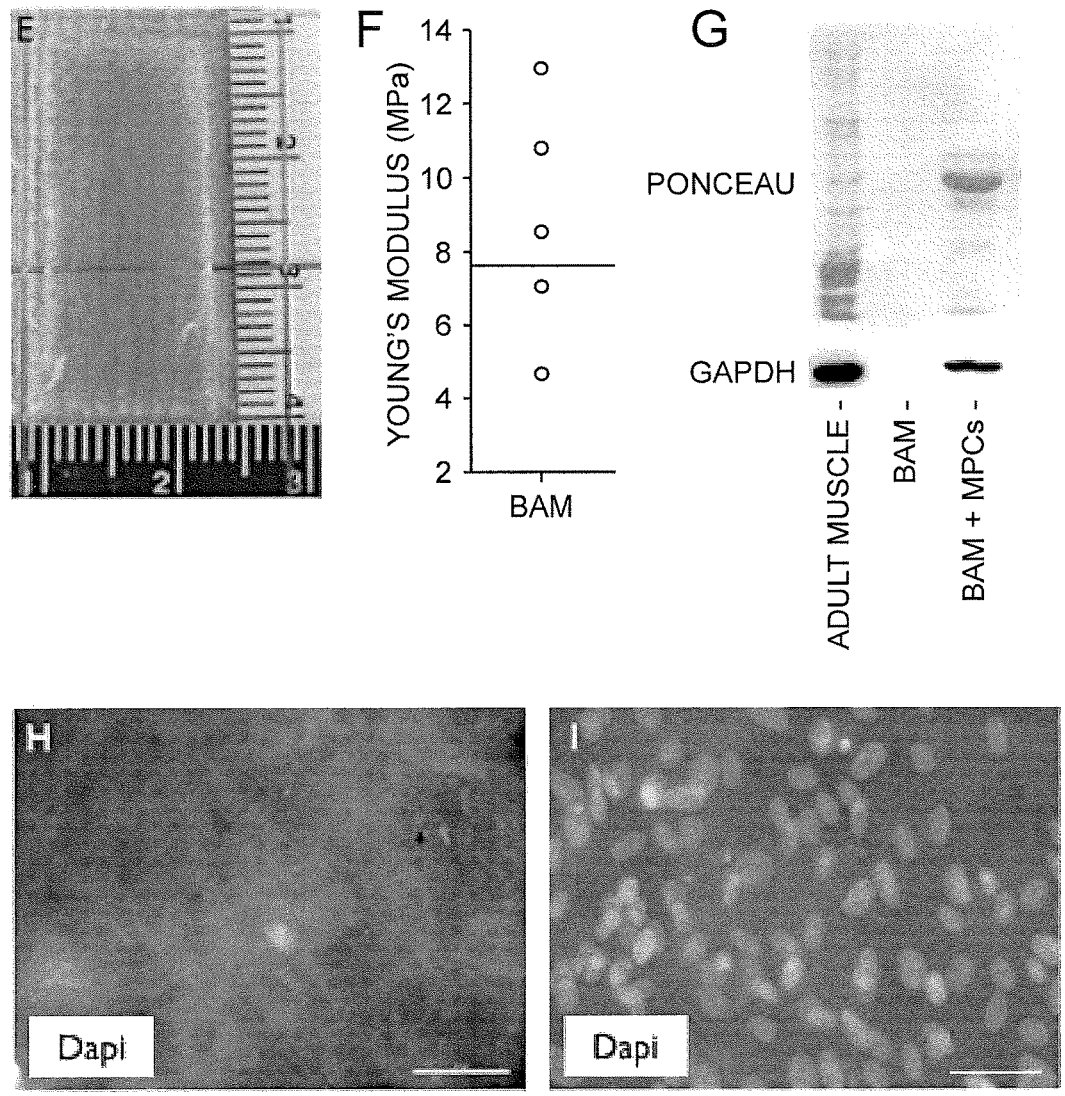

Precursor Cell Characterization. Cells from primary culture were passaged twice, seeded on glass chamber slides with no coating, and incubated for one day in proliferation media. At this time and under these conditions, the percentage of cells expressing Pax7, MyoD, and desmin was ~36, 34, and 21% respectively (FIG. 8). This analysis performed on uncoated glass chamber slides may underestimate the percentage of the myogenic cell population on BAM scaffolds, which provide a more elastic surface than either glass or plastic.

Figure 9:
FIG. 9. Cellular morphology and protein expression characteristics of BAM-supported TEMR constructs developed under varying culture conditions. Cell morphology of TEMR constructs generated under "Proliferation", "Differentiation", or "Mixed" culture conditions (See Methods in Example 3) are depicted in A, B, & C, respectively (400× images). For the generation of the "Mixed" construct group, a second batch of MPCs was added to an underlying layer of MPCs (i.e., "Differentiation" constructs). To confirm adherence of the second MPC batch, these cells were loaded with cytoplasmic fluorescent dye (Cm-Dio) and then visualized following preconditioning (D & E). The number of nuclei (F) and the number of multinucleated cells (G) were quantitated for each construct type (See methods, *≠Proliferation; #≠Differentiation, p<0.05). Muscle-specific protein expression of TEMR constructs was characterized via Western blot (H). The optical densities of specified proteins were normalized to that of Gapdh for statistical comparisons among groups (I; * Significantly different from Proliferation, p<0.05). Protein expression of each construct type is summarized (J).
Figure 9:
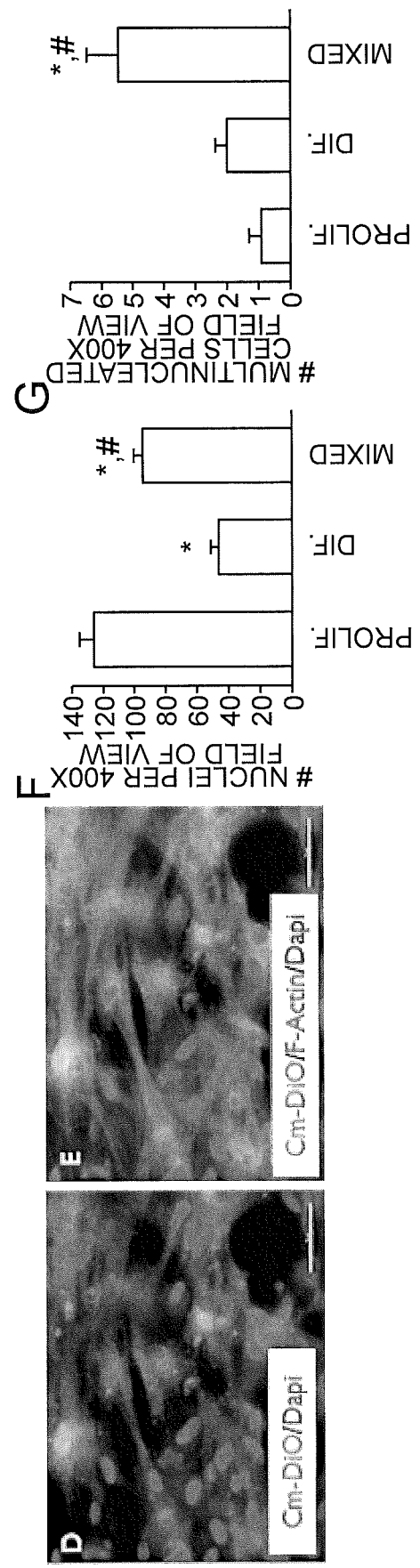
Figure 9:
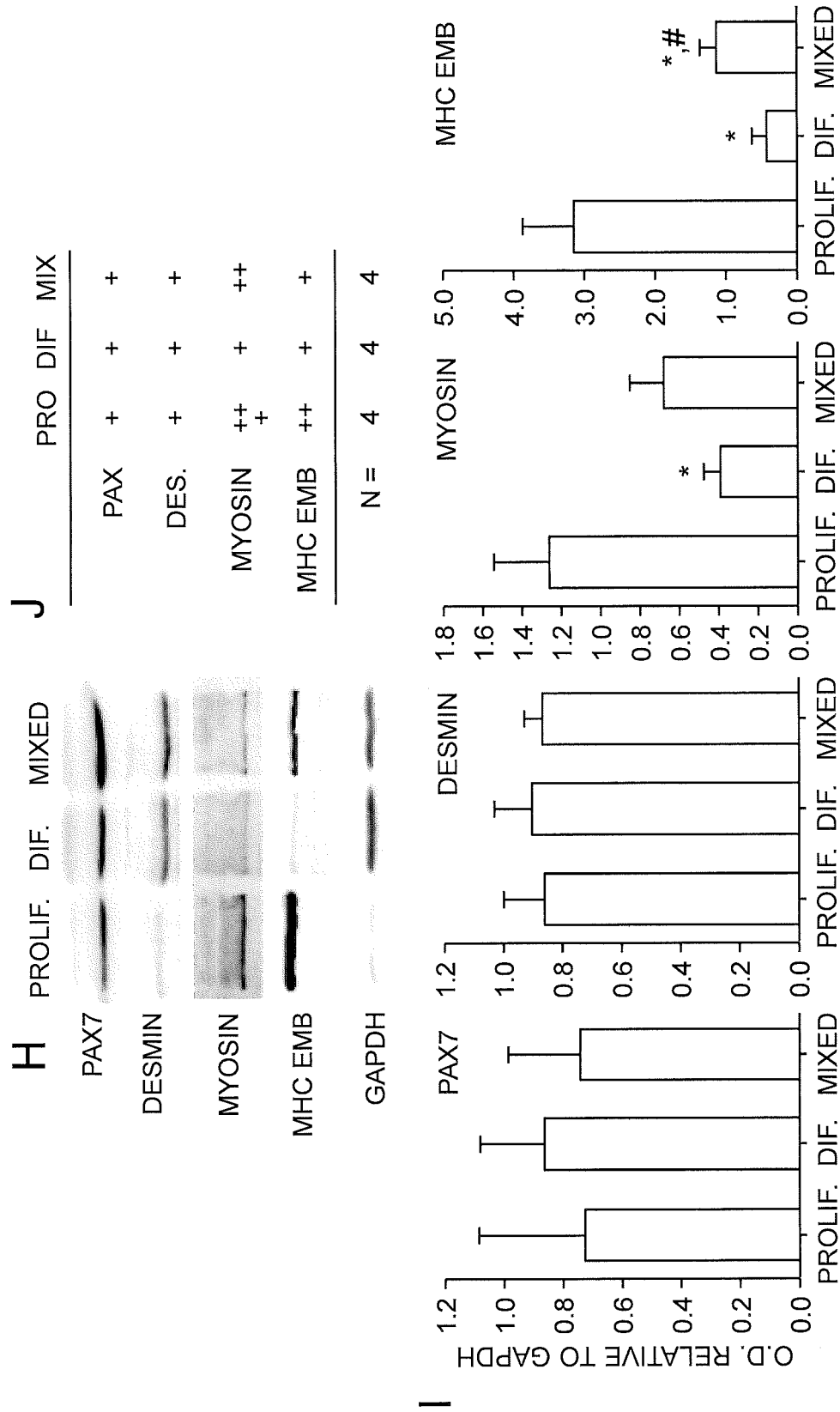

TEMR Construct Characterization Prior to Implantation. TEMR constructs generated under "Proliferation", "Differentiation", or "Mixed" culture conditions exhibited different morphological characteristics (FIG. 9). Under proliferation conditions MPCS appeared unfused and were not aligned (FIG. 9A), while under differentiation conditions (serum starvation+uniaxial mechanical strain) MPCs exhibited an elongated and aligned morphology, however, the number of multinucleated cells was not significantly increased (FIG. 9G). Also, the total number of nuclei was significantly reduced following differentiation culture conditions. The addition of a second batch of MPCs to an underlying layer of differentiating cells (i.e., "Mixed" culture conditions) promoted an elongated and aligned cellular morphology, a partial restoration of the total number of nuclei on the scaffold, and a significant increase in the number of multinucleated cells. It is likely that the latter observation was achieved via fusion of a portion of the second batch of MPCs with the underlying cellular layer.

Muscle protein characterization revealed that all construct types expressed both immature and mature muscle markers, suggesting that each construct type is comprised of MPCs under multiple states of differentiation and maturation. All constructs expressed similar Pax7 and desmin protein expression relative to gapdh (FIG. 9I). However, TEMR constructs generated under differentiation conditions expressed significantly less myosin and embryonic myosin heavy chain ($MHC_{emb}$) relative to gapdh than under proliferation conditions. The addition of MPCs under the mixed culture conditions promoted partial restoration of myosin and $MHC_{emb}$.

In Vitro Isometric Strength Analysis. Uninjured or injured LD muscles that received no repair (NR) or repair with TEMR construct underwent in vitro isometric force-frequency testing either one or two months post-injury. For NR muscles, peak isometric twitch force ($P_t$), maximal isometric force at 80 Hz stimulation ($P_{80Hz}$), and peak tetanic force ($P_0$) were significantly reduced by ~66, 71, and 75% compared to uninjured values one month post-injury (FIG. 10; Table 1). At two months post-injury, the NR group exhibited similar functional deficits for $P_1$ and $P_{80Hz}$ (~77 & 75%, respectively). Although, some recovery of $P_0$ from one to two months post-injury was observed for NR muscles (FIG.

10; Table 1), a continued ~67% functional deficit of $P_O$ two months post-injury indicates a critical size defect was achieved in this study using this VML injury model.

Functional recovery mediated via TEMR construct repair was construct type and time dependent. At one month post-injury, TEMR constructs generated under both proliferation and mixed culture conditions exhibited improved LD function compared to NR values. For example, at this time $P_t$, $P_{80Hz}$, and $P_O$ were greater by ~96, 106, 111% for proliferation and by ~50 (p=0.276), 128, and 120% for mixed groups. In contrast, $P_t$, $P_{80Hz}$, and $P_O$ produced by the differentiation TEMR construct group were not significantly different from NR (FIG. 10; Table 1). Moreover, at this time the proliferation and mixed groups produced similar Pa to each other (FIG. 10; Table 1) and ~36 (p=0.075) and 41% greater $P_O$ than the differentiation group. Lastly, NR, differentiation, and mixed groups exhibited a significantly leftward shift in the force-frequency curve (i.e., $EC_{50}$<Uninjured; Table 1), while the proliferation group was similar to uninjured muscle.

functional recovery was TEMR construct dependent. From one to two months, the differentiation and mixed TEMR construct groups exhibited a ~39 and 28% improvement in $P_O$, respectively, however, the proliferation group showed no significant improvement (i.e., 0.2%) over this time. Lastly, the leftward shift in the force-frequency curves observed at one month post-injury for NR, differentiation, and mixed groups was rectified at two months.

Absolute forces were normalized to estimated physiological cross sectional area to calculate specific force (N·cm$^2$). There were no significant differences among experimental groups at either one or two months post-injury and all experimental groups produced significantly less specific $P_O$ than uninjured muscles (Table 1). LD muscle wet weight was consistently greater for all TEMR construct groups at one and two months post-injury compared to uninjured and NR groups, while LD muscle length was similar among all groups.

For a subset of muscles, peak caffeine contracture force was measured two months post-injury. All experimental

TABLE 1

LD muscle morphological characteristics and in vitro isometric force parameters

| | | One Month Post-Injury | | | | Two Months Post-Injury | | | | |
|---|---|---|---|---|---|---|---|---|---|---|
| Sample Size | Uninjured 22 | NR 5 | Prolif 6 | Dif 7 | Mixed 8 | NR 4 | Prolif 6 | Dif 7 | Mixed 8 | ANOVA (p) |
| Muscle Characteristics | | | | | | | | | | |
| Wet Weight (mg) | 90.3 ± 3.7 | 102.4 ± 11.8 | 166.1 ± 10.1$^{a,b}$ | 154.8 ± 14.1$^{a,b}$ | 162.0 ± 14.6$^{a,b}$ | 86.6 ± 11.5 | 152.0 ± 14.3$^{a,b}$ | 151.6 ± 23.5$^{a,b}$ | 152.8 ± 17.0$^{a,b}$ | <0.001 |
| $L_o$ (mm) | 34.9 ± 0.8 | 33.3 ± 1.7 | 33.8 ± 1.4 | 36.2 ± 1.5 | 34.9 ± 1.4 | 32.6 ± 0.8 | 31.0 ± 2.2 | 31.9 ± 1.3 | 32.1 ± 0.6 | 0.099 |
| Isometric Force Parameters | | | | | | | | | | |
| $P_{t\,meas}$, mN | 46.8 ± 3.5 | 16.1 ± 2.6$^a$ | 31.6 ± 2.7$^{a,b}$ | 19.8 ± 3.2$^a$ | 24.1 ± 5.4$^a$ | 10.6 ± 2.4$^a$ | 21.9 ± 4.9$^a$ | 20.0 ± 2.9$^a$ | 39.0 ± 4.3$^{b,*}$ | <0.001 |
| $P_{80\,Hz\,meas}$, mN | 212.2 ± 8.9 | 61.0 ± 8.3$^a$ | 125.5 ± 9.6$^{a,b}$ | 95.6 ± 13.2$^a$ | 138.8 ± 14.6$^{a,b}$ | 54.2 ± 9.9$^a$ | 102.0 ± 16.4$^{a,b}$ | 104.9 ± 10.7$^{a,b}$ | 135.5 ± 17.1$^{a,b}$ | <0.001 |
| $P_{o\,meas}$, mN | 374.4 ± 12.1 | 93.1 ± 17.3$^a$ | 196.9 ± 13.0$^{a,b}$ | 144.4 ± 21.9$^a$ | 203.2 ± 19.7$^{a,b,d}$ | 123.3 ± 19.1$^{a,*}$ | 197.2 ± 24.0$^{a,b}$ | 200.1 ± 16.3$^{a,b,*}$ | 259.3 ± 19.3$^{a,b,c,d,*}$ | <0.001 |
| $EC_{50}$, Hz | 78.7 ± 1.6 | 68.7 ± 4.4$^a$ | 76.2 ± 3.6 | 68.4 ± 4.4$^a$ | 68.5 ± 3.6$^a$ | 87.0 ± 3.3$^*$ | 81.9 ± 2.3 | 81.8 ± 1.5$^*$ | 85.3 ± 4.2$^*$ | <0.001 |
| n coefficient | 4.1 ± 0.2 | 3.6 ± 0.2 | 4.6 ± 0.6 | 3.6 ± 0.4 | 4.4 ± 0.5 | 4.4 ± 0.3 | 6.1 ± 1.4 | 4.2 ± 0.5 | 4.5 ± 0.3 | 0.127 |
| Specific $P_{o\,meas}$, N-cm$^2$ | 15.6 ± 0.7 | 3.2 ± 0.5$^a$ | 4.2 ± 0.2$^a$ | 3.4 ± 0.7$^a$ | 4.9 ± 0.7$^a$ | 5.1 ± 1.0$^a$ | 4.5 ± 0.8$^a$ | 4.7 ± 0.3$^a$ | 6.4 ± 1.0$^a$ | <0.001 |
| Caffeine, mN | 112.5 ± 6.3 | — | — | — | — | 41.3 ± 3.7$^a$ | 83.7 ± 10.8$^{a,b}$ | 67.3 ± 5.4$^{a,b}$ | 86.6 ± 5.5$^{a,b}$ | <0.001 |

Values are means ± SE. LD muscle sample sizes are for measured electrical stimulation force parameters.
$L_o$ is the optimal muscle length coinciding with peak twitch force.
Measured isometric twitch ($P_t$), tetanic force at 80 Hz ($P_{80\,Hz}$), and peak tetanic ($P_o$) force were elicted using direct electrical stimulation (0.2 ms pulse width; 30 V).
$EC_{50}$ is the stimulation frequency at which half of the rise in amplitude of force occurred.
The n coefficient is the slope of the linear portion of the force-frequency curves depicted in FIG 3. Absolute $P_o$ was normalized by physiological cross-sectional area (see methods) to determine specific force. Following force-frequency testing a subset of muscles performed an isometric caffeine (50 mM) contracture test.
Denotations indicate statistically significantly different group means (p < 0.05):
$a \neq$ Uninjured;
$b \neq$ NR at same post-injury time;
$c \neq$ Proliferation at same post-injury time;
$d \neq$ Differentiation at same post-injury time;
$* \neq$ 1 month for same experimental group.

Figure 10:
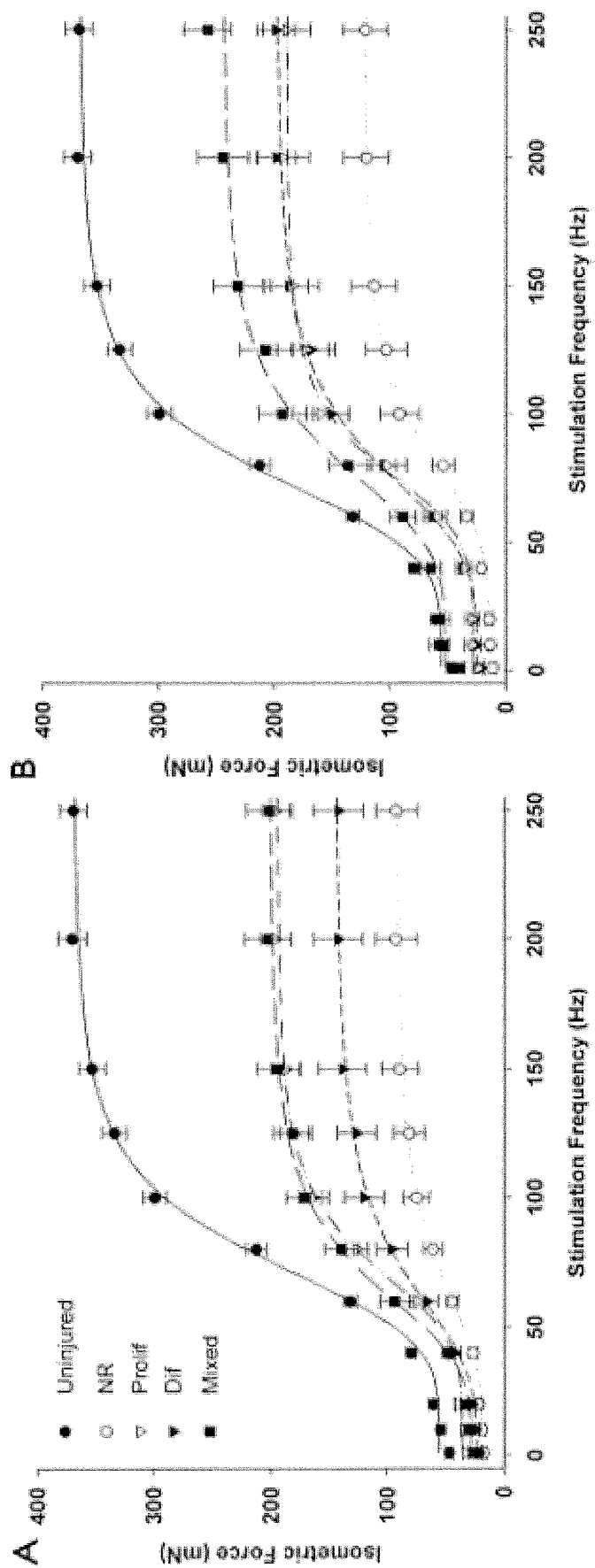
FIG. 10. LD muscle in vitro isometric force recovery following VML injury is dependent on TEMR construct type. Uninjured and injured but non-repaired (NR) or TEMR construct (3 types, Proliferation, Differentiation, and Mixed)-repaired LD muscles were tested using direct muscle stimulation at 35° C. in an organ bath (See Methods in Example 3). Isometric force as a function of stimulation frequency was assessed for all experimental conditions at either one (A) or two (B) months post-injury. Force-frequency curves were fit with a Hill equation as described in the methods. Peak isometric tetanic force functional deficits relative to the uninjured group mean was calculated for all experimental groups at one (C) and two (D) months. For each post-injury time, *≠ to NR while #≠ to all other groups (p<0.05). Values are expressed as means±SE. Sample sizes for each group at each post-injury time are listed in Table 1.
Figure 10:
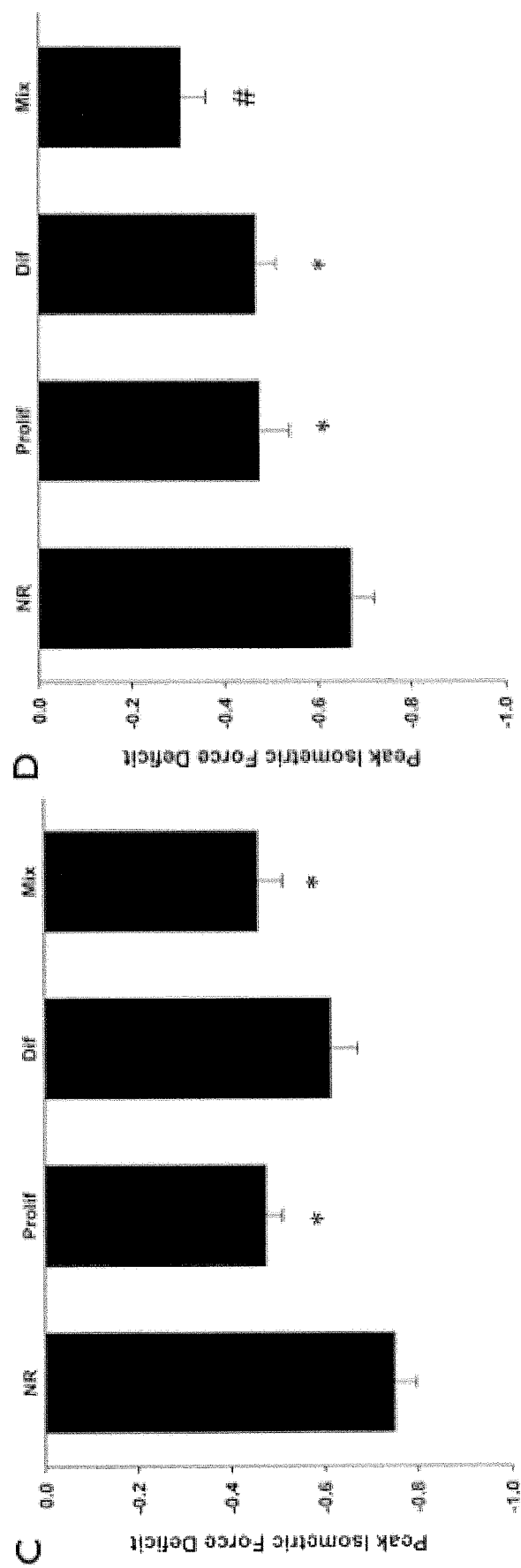

At two months post-injury, all TEMR construct groups produced significantly greater $P_{80Hz}$, and $P_O$ than NR, although only the mixed group produced significantly greater $P_t$ (FIG. 10; Table 1). However, the magnitude of functional recovery was TEMR construct dependent. For instance, $P_O$ produced by proliferation, differentiation, and mixed groups was ~60, 62, and 110% greater than NR at two months, with the mixed group producing greater $P_O$ than both proliferation and differentiation groups (e.g., ~30%>Differentiation). Additionally, the time-course of groups were significantly reduced compared to uninjured controls (Table 1). However, all TEMR construct groups produced similar contracture forces to each other and greater contracture force than the NR group. Specifically, proliferation, differentiation, and mixed groups produced ~103, 63, and 110% greater contracture force than NR, respectively.

Figure 11:
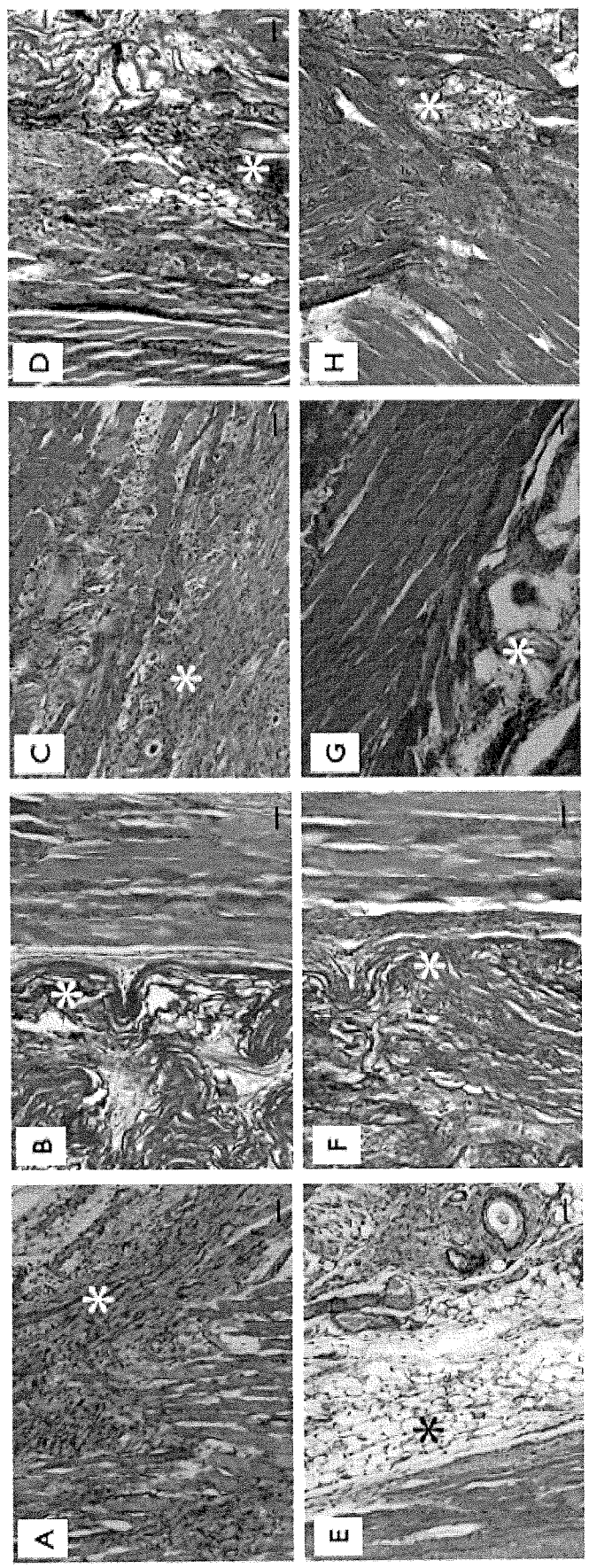
FIG. 11. LD muscle tissue morphology after VML injury and immediate repair with TEMR constructs. VML injured LD muscles that were either not repaired (A & E) or repaired with "proliferation" (B & F), "differentiation" (C & G), or "mixed" (D & H) TEMR constructs were retrieved one (A-D) and two (E-H) months post-injury and stained using Masson's Trichrome (tissue, Collagen, Nuclei). *Marker of area of initial injury (A & E) or presumptive BAM collagen deposition (B-E & F-H). Images are 200× magnification with the scale bar=50 μm.
Figure 12:
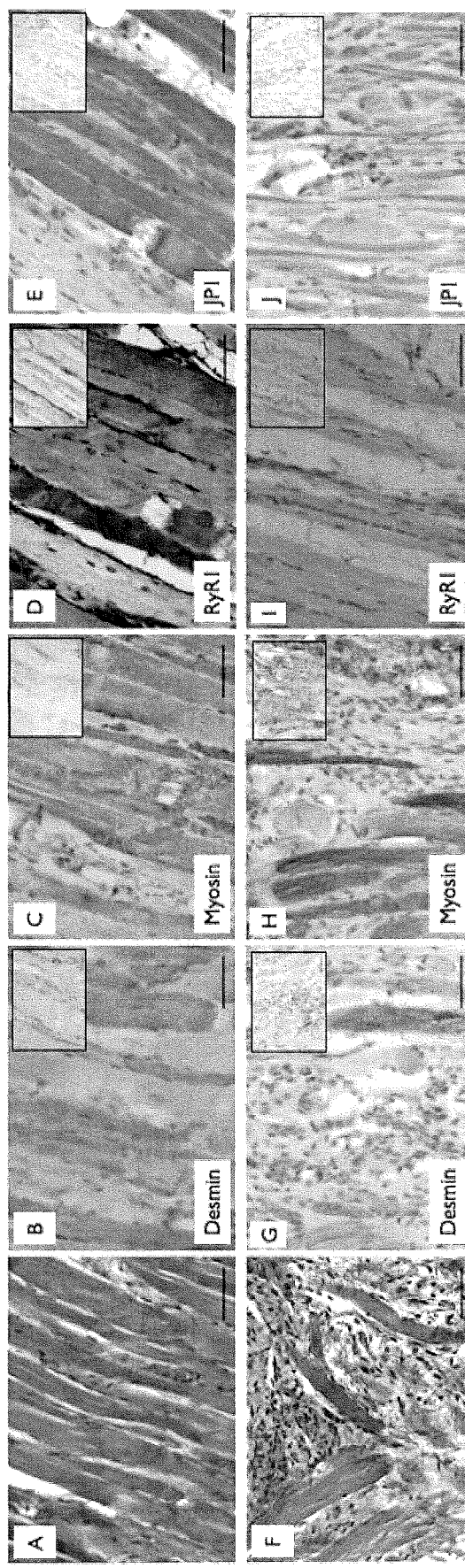
FIG. 12. Functional protein expression in regenerating muscle fibers and putative neo-tissue two months after TEMR construct treatment of VML injured LD muscle. Images are representative of tissue regeneration and formation observed in all all three types of TEMR construct-repaired LD muscles. Masson's trichrome staining and immunohistochemical staining for functional proteins is illustrated at the interface between the remaining native tissue and the TEMR construct (A-E) as well as for independent tissue formed in BAM scaffolding (F-J). Insets show negative control staining for the primary antibody. Images are 400× magnification with the scale bar=50 μm.

Cell and Tissue Morphology. Tissue and cell morphology of VML injured LD muscles with and without TEMR construct repair were qualitatively characterized. Specifically, the area of VML injury, where the implanted TEMR constructs interface with the remaining tissue was of specific interest and is illustrated in FIG. 11 for NR and TEMR construct repair groups at one and two months post-injury. In agreement with functional deficits observed, the NR group exhibited gross tissue disruption, marked by the presence of small muscle fibers, increased collagen deposition, and monocytes indicating a continued immune response at one month post-injury. Two months post-injury, the NR muscle appears to have completed the innate degenerative and regenerative response to the VML injury. At this time, the NR tissue shows little monocyte presence, improved muscle fiber organization, and collagen and adipose deposition at the site of injury.

Figure 13:
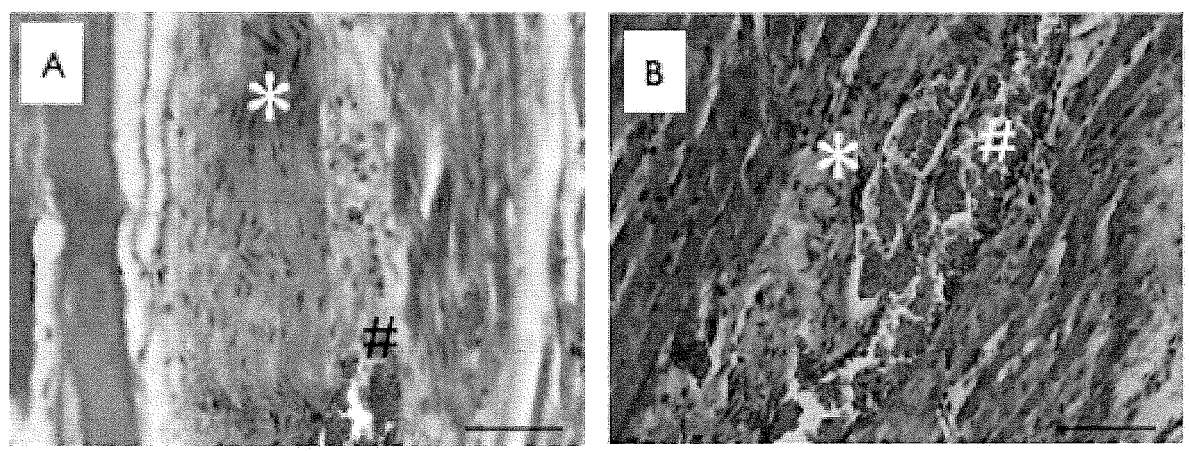
FIG. 13. Presence of vascular and neural structures one month after TEMR construct treatment of VML injured LD muscle. Images are representative of vascular (#) and neural (*) structures that were identified via characteristic morphology and were observed in all TEMR construct groups one month post-injury. Images are 400× magnification; Scale bar=50 μm.

In all cases, TEMR construct implantation resulted in improved tissue morphology compared to NR muscles. At one and two months post-injury the muscle fibers at the initial site of injury present qualitatively less signs of damage, disruption, and monocyte presence in TEMR construct repaired versus NR tissue (FIG. 11). There were, however, distinct differences in tissue morphology among TEMR construct groups. For example, while the muscle fibers at the interface were either regenerated or repaired by one month post-injury for the proliferation group, the remaining BAM scaffold was mostly devoid of a cellular presence (FIG. 11B). A similar morphology was also observed at two months post-injury with TEMR construct implantation generated under proliferation conditions (FIG. 11F). In contrast, a cellular presence within the scaffold was observed in both the differentiation and mixed construct groups. And, from one to two months there appeared to be an increase in muscle tissue formation both at the site of injury (FIGS. 11C & G) and within the scaffold independent of the primary muscle tissue (FIGS. 11D & H). Lastly, we also observed a marked vascular and neural presence at the tissue-scaffold interface one month post-injury when TEMR constructs were implanted, however, there was no obvious difference in the occurrence of these structures among construct types (FIG. 13). As illustrated, the neural and vascular structures were associated with regenerating muscle fibers in most cases.

Functional Protein Expression. To determine if regenerating or newly formed muscles fibers were capable of contributing to functional recovery, TEMR construct-repaired LD muscles retrieved two months post-injury were stained using IHC for a host of key proteins required for force production and transmission. Two areas of interest within the repaired LD muscles were identified: 1) The area of initial VML injury at the interface between TEMR constructs and the remaining native tissue (FIG. 12A-E); And 2) at sites of tissue formation within BAM scaffolding independent from the interface (FIG. 12F-J). For all construct groups, muscle fibers in each of these areas stained positively (determined by negative control and striated appearance) for desmin, myosin, ryanodine receptor 1 (RyR1), and junctophilin 1 (JP1).

Figure 14:
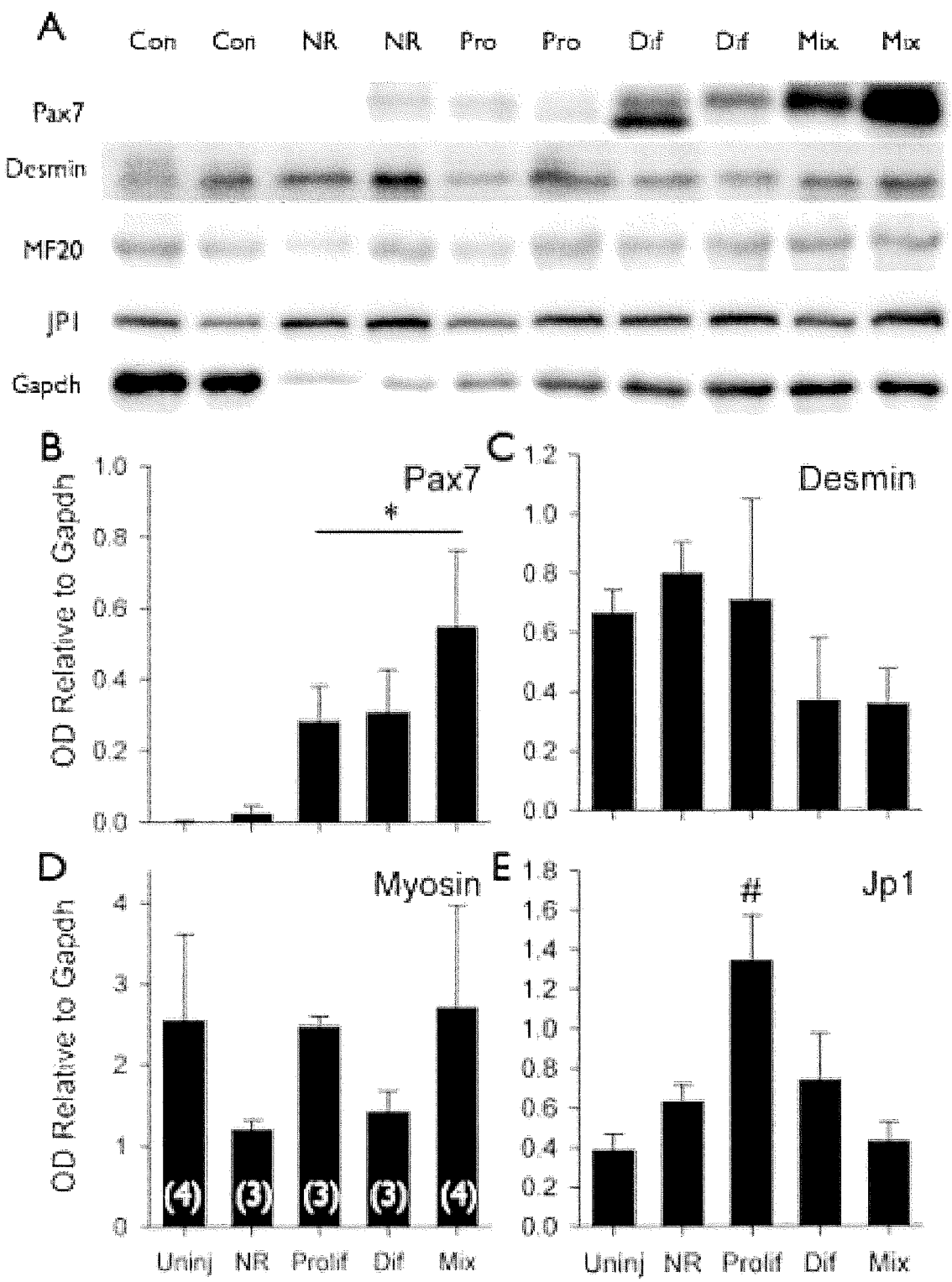
FIG. 14. LD muscle protein expression two months post-injury. A) LD muscles were probed for Pax7, desmin, myosin (MF20), junctophilin 1 (JP1), and gapdh using SDS-PAGE and Western blotting (See methods in Example 3). B-D) Optical density was determined for each band and normalized to gapdh. *, Significantly different from uninjured; #, Significantly different from all other groups ($p<0.05$). Values are expressed as means±SE. Sample sizes for each group are listed in parentheses in panel D.

The relative content of specific muscle proteins involved in force production and transmission can be reduced in injured muscle leading to functional deficits. In this study, relative protein content of desmin, jp1, and myosin (normalized to gapdh) was quantified in whole or myofibrillar (myosin only) protein homogenates from uninjured and VML injured LD muscles two months post-injury (FIG. 14). No differences among uninjured, NR, and TEMR construct groups were observed for either desmin or myosin. In comparison to all other treatment groups, JP1 was elevated for TEMR constructs generated under proliferation conditions, although it is unclear what the physiological relevance of this increase is.

Pax7 Expression in TEMR Construct Repaired LD muscle. Lastly, while the muscle fibers at the interface appear to have completed or nearly completed the regenerative response two months after injury (FIGS. 11 & 12) in TEMR construct-repaired LD muscles, fibers localized to the scaffold often appear smaller in diameter, suggesting that the regenerative response is not completed in this area (FIG. 12G-J). Because Pax7 expression, a satellite cell marker, increases in regenerating muscle following injury, protein expression of this regenerative marker was determined in whole LD muscle homogenates (FIG. 14). In comparison to uninjured values, Pax7 expression was significantly elevated for all TEMR construct groups, but not for the NR group.

The foregoing is illustrative of the present invention, and is not to be construed as limiting thereof. The invention is defined by the following claims, with equivalents of the claims to be included therein.

That which is claimed is:

1. A muscle construct comprising elongated multi-nucleated muscle cells or fibers in multilayer configuration on a support, wherein said support comprises collagen, and wherein the muscle construct is produced by a process of:
    seeding precursor muscle cells onto the support wherein the support is a decellularized tissue support, and culturing the cells in a substantially static position in vitro, then
    cyclically stretching and relaxing the precursor muscle cells for a time sufficient to produce organized skeletal muscle tissue, wherein said cyclically stretching and relaxing comprises:
        (a) cyclically stretching and relaxing said support three times per minute along an axis during a first time period of from 2 to 10 minutes in duration, wherein the stretching comprises extending said support to a dimension of between 5% and 15% greater in length than said static position; and then
        (b) maintaining said support in the substantially static position during a second time period of from 20 to 90 minutes in duration; and then
        (c) repeating steps (a) and (b) for a number of times sufficient to enhance the functionality of the muscle tissue or produce organized skeletal muscle tissue on said support from said precursor muscle cells;
    reseeding said organized skeletal muscle tissue by contacting additional precursor muscle cells to said organized skeletal muscle tissue on said support, wherein said reseeding is carried out under static conditions; and then
    repeating said step of cyclically stretching and relaxing said muscle cells for a time sufficient to enhance the density of said organized skeletal muscle tissue on said support, to form said muscle construct,
    wherein said additional precursor muscle cells fuse with said precursor muscle cells which have been seeded to form multinucleated myotubes, and
    wherein said cyclically stretching and relaxing does not result in an increase in myosin, as compared to a muscle construct comprising precursor muscle cells which have been seeded on a support comprising collagen in vitro that has not been subjected to the cyclically stretching and relaxing, during a time of from 5 to 7 days of said cyclically stretching and relaxing.

2. The muscle construct of claim 1, wherein said repeating steps (a) and (b) is carried out for a time of five days to three weeks.

3. The muscle construct of claim 1, wherein said support is porous.

4. The muscle construct of claim 1, wherein said support is from 20 µM to 1000 µM thick.

5. The muscle construct of claim 1, wherein said cyclically stretching and relaxing results in a decrease in embryonic myosin heavy chain (MHC), as compared to a muscle construct comprising precursor muscle cells which have been seeded on a support comprising collagen in vitro that has not been subjected to the cyclically stretching and relaxing.

6. The muscle construct of claim 1, wherein said construct comprises from 5 to 400 multinucleated cells per square millimeter of tissue or support surface area.

7. The muscle construct of claim 1, wherein said construct further comprises activated satellite cells or myoblasts.

8. The muscle construct of claim 1, wherein said muscle cells or fibers express acetylcholine receptors.

9. The muscle construct of claim 1, wherein said muscle cells or fibers comprise aggregated acetylcholine receptors.

10. The muscle construct of claim 1, wherein said muscle cells or fibers comprise aggregated acetylcholine receptors forming a pretzel shape characteristic of motor end plates.

11. The muscle construct of claim 1, wherein said construct is suturable.

12. The muscle construct of claim 1, wherein the precursor muscle cells are primary muscle cells harvested from a donor and passaged in vitro once, twice, or three times.

13. The muscle construct of claim 1, wherein the second time period is from 50 to 58 minutes in duration.

14. A method of treating a skeletal muscle injury in a patient in need thereof comprising grafting the muscle construct of claim 1 into said patient.

* * * * *

UNITED STATES PATENT AND TRADEMARK OFFICE
CERTIFICATE OF CORRECTION

PATENT NO. : 11,324,857 B2
APPLICATION NO. : 15/378534
DATED : May 10, 2022
INVENTOR(S) : Christ et al.

It is certified that error appears in the above-identified patent and that said Letters Patent is hereby corrected as shown below:

In the Specification

Column 3, Line 47: Please correct "f SD." to read -- ± SD. --

Column 10, Line 31: Please correct "DAN" to read -- DAPI --

Column 11, Line 54: Please insert the following after the Table:
-- Seeding Media
DMEM (Low Glucose)
15% FBS
1% Antibiotic/Antimycotic (AA)
Differentiation Media
F-10 Media
2% HS
1% AA
Bioreactor Seeding Media
DMEM (Low Glucose)
15% FBS
2% Antibiotic/Antimycotic (AA) --

Column 18, Line 65: Please correct "$P_1$" to read -- $P_t$ --

Signed and Sealed this
Eleventh Day of October, 2022

Katherine Kelly Vidal
*Director of the United States Patent and Trademark Office*